(12) United States Patent
Pfluecker et al.

(10) Patent No.: US 8,753,684 B2
(45) Date of Patent: Jun. 17, 2014

(54) PARTICULATE UV PROTECTION AGENT

(75) Inventors: Frank Pfluecker, Darmstadt (DE);
Bernd Hirthe, Tönisvorst (DE)

(73) Assignees: Merck Patent GmbH, Darmstadt (DE);
Sachtleben Chemie GmbH, Duisburg (DE)

( * ) Notice: Subject to any disclaimer, the term of this patent is extended or adjusted under 35 U.S.C. 154(b) by 26 days.

(21) Appl. No.: 13/524,179

(22) Filed: Jun. 15, 2012

(65) Prior Publication Data
US 2012/0258154 A1 Oct. 11, 2012

Related U.S. Application Data

(63) Continuation of application No. 12/524,741, filed as application No. PCT/EP2008/000496 on Jan. 23, 2008, now abandoned.

(30) Foreign Application Priority Data

Jan. 29, 2007 (DE) .......... 10 2007 005 186

(51) Int. Cl.
| | | |
|---|---|---|
| A61K 9/14 | (2006.01) | |
| A61K 8/02 | (2006.01) | |
| A61K 47/00 | (2006.01) | |
| A61K 8/49 | (2006.01) | |
| A61K 33/06 | (2006.01) | |

(52) U.S. Cl.
USPC .......... 424/489; 424/401; 424/439; 424/70.9; 424/682

(58) Field of Classification Search
None
See application file for complete search history.

(56) References Cited

U.S. PATENT DOCUMENTS

| | | | |
|---|---|---|---|
| 5,643,592 A | | 7/1997 | Jacobson et al. |
| 6,086,928 A | * | 7/2000 | Stevens et al. .......... 426/92 |
| 6,599,351 B1 | | 7/2003 | Rentschler et al. |
| 2005/0249682 A1 | | 11/2005 | Buseman-Williams et al. |
| 2006/0194057 A1 | * | 8/2006 | Pfluecker et al. .......... 428/404 |
| 2008/0031832 A1 | | 2/2008 | Wakefield et al. |
| 2009/0275686 A1 | * | 11/2009 | Kastner et al. .......... 524/410 |

FOREIGN PATENT DOCUMENTS

| | | |
|---|---|---|
| DE | 198 26 379 | 12/1999 |
| EP | 1544256 | * 12/2004 |
| GB | 1 162 799 | 8/1969 |
| GB | 1 222 955 | 2/1971 |
| WO | WO-99 60994 | 12/1999 |
| WO | 2005072680 A2 | 8/2005 |
| WO | WO-2007 141342 | 12/2007 |
| WO | WO-2008 015056 | 2/2008 |

OTHER PUBLICATIONS

Wakefield, G. et al., "Sonnenschutzmittel und Kosmetika mit Mangan dotierten Titanoxid-Nanopartiken," SOFW—Journal, 2005, Bd. 131, pp. 60-64.
Recker, K. et al., "Kristalle: Einkristallzuchtung," Ullmanns Encyklopadie der technischen Chemie, 1975, Bd. 15, pp. 117.
International Search Report for PCT/EP2008/000496 dated Jul. 31, 2009.

* cited by examiner

*Primary Examiner* — Daniel Sullivan
*Assistant Examiner* — Melissa Javier
(74) *Attorney, Agent, or Firm* — Millen, White, Zelano & Branigan, P.C.

(57) ABSTRACT

The present invention relates to particulate UV protection agents which are obtainable by hydrothermal treatment of a particulate metal oxide and subsequent application of a manganese oxide coating, and to the preparation and use thereof. The present invention furthermore relates to novel compositions, in particular for topical application, which are intended, in particular, for light protection of the skin and/or hair against UV radiation and free-radical-induced stress, and to the use thereof in the above-mentioned cosmetic application.

15 Claims, 3 Drawing Sheets

Example 3a    Example 3b    Example 7

PARTICULATE UV PROTECTION AGENT

This application is a continuation application of U.S. Ser. No. 12/524,741, filed Jul. 28, 2009, now abandoned.

The present invention relates to particulate UV protection agents, to aqueous or oily dispersions comprising these particulate UV protection agents, to the preparation and use thereof. The present invention furthermore relates to novel compositions for topical application which are intended, in particular, for light protection of the skin and/or hair against UV radiation (compositions which are referred to below simply as sunscreens), and to the use thereof in the above-mentioned cosmetic application.

It is known that the human epidermis can be tanned by light radiation having a wavelength in the range from 280 to 400 nm and that radiation having a wavelength in the range from 280 to 320 nm, which is known under the term UV-B, causes erythema and skin burning, which may be detrimental to the formation of a natural tan. The UV-B radiation should therefore be filtered out.

It is furthermore known that UV-A radiation having a wavelength in the range from 320 to 400 nm, which tans the skin, can cause a change in the skin, in particular in the case of sensitive skin or skin which is exposed continuously to sunlight. UV-A radiation causes, in particular, a loss in skin elasticity and wrinkling, which results in premature ageing. It favours the triggering of erythema formation or increases this reaction in some people, and it can even be the cause of toxic or allergic reactions triggered by light. It is therefore desirable also to filter out the UV-A radiation.

In cosmetics, numerous organic sunscreen filters which are able to absorb the harmful UV-A radiation more or less selectively have been indicated to date.

A group of UV-A filters which is particularly interesting in this respect currently consists of dibenzoylmethane derivatives, in particular 4,4'-methoxy-tert-butyldibenzoylmethane, which have a strong intrinsic absorption capacity. These dibenzoylmethane derivatives, which are currently well-known products per se as filters which are effective in the UV-A region, are described, in particular, in the French patent applications FR-A-2 326 405 and FR-A-2 440 933 and in European patent application EP-A-0 114 607. 4,4'-Methoxy-tert-butyldibenzoylmethane is in addition currently commercially available from Merck under the trade name Eusolex® 9020.

These dibenzoylmethane derivatives can be combined with a UV-B filter in order to obtain complete protection over the entire spectrum of sunlight in the UV region.

It is furthermore known that the addition of an inorganic pigment and in particular of a titanium dioxide ($TiO_2$) pigment enables the light-protection properties of sunscreens comprising UV filters to be improved.

The combination of organic UV filters, such as, for example, dibenzoylmethane derivatives, and particulate metal oxides is therefore highly valued in the area of sunscreens.

Furthermore, titanium dioxide can have a pro-oxidative action after excitation by UV radiation and thus contribute to the formation of hydroxyl or peroxide free radicals. These effects are undesired, in particular, on use of titanium dioxide in cosmetic sunscreens since the skin may be stressed by free radicals of this type.

It is furthermore observed that these phenomena are particularly pronounced in the case of micronised $TiO_2$.

WO 99/60994 proposes doping titanium dioxide with $Mn^{3+}$ ions in order to reduce the pro-oxidative properties.

Surprisingly, it has now been found that it is possible to suppress the pro-oxidative properties if metal oxides have a manganese-containing coating.

The present invention therefore relates firstly to a UV protection agent, where the UV protection essentially emanates from a particulate metal oxide, characterised in that the metal oxide has a manganese-containing coating.

The coating is preferably a manganese-containing coating and/or a silicon dioxide, manganese dioxide, cerium oxide or aluminium oxide or silicon hydroxide, manganese hydroxide, cerium hydroxide or aluminium hydroxide coating, or a mixture thereof.

The manganese-containing coating consists of manganese-containing compounds, which, for the purposes of the invention, are particularly preferably manganese oxides, for example manganese dioxide and/or manganese hydroxides.

In a particularly preferred variant of the invention, the UV protection agent is obtainable by hydrothermal treatment of a particulate metal oxide and subsequent application of at least one coating.

Hydrothermal treatment is taken to mean the heating of an aqueous solution or suspension or dispersion in a closed container, optionally under pressure (cf. also Ullmanns Enzyklopädie der Technischen Chemie [Ullmann's Encyclopaedia of Industrial Chemistry], 4th Edition, 1978, Volume 15, pp. 117 ff: K. Recker, Einkristallzüchtung [The Growing of Single Crystals]).

For the purposes of a variant of the invention, a particulate UV protection agent is preferably taken to mean a particulate metal oxide having a manganese-containing silicon dioxide or aluminium oxide coating.

The crystallite size of the particulate metal oxide in the particulate UV protection agent, determined by the Scherrer method, is usually in the range from 5 nm to 100 nm, preferably in the range 8 to 50 nm and particularly preferably below 25 nm. The dimensions of the particulate metal oxide, which can be determined in a transmission electron microscope, are usually a length of 5 to 150 nm and a width of 5 to 60 nm. The length is preferably in the range from 20 to 60 nm and the width in the range from 8 to 30 nm.

The particulate metal oxides used here for the use according to the invention are, in particular, titanium dioxide, iron oxides, zinc oxide or also cerium oxides, where titanium dioxide is particularly preferred in accordance with the invention as metal oxide since it achieves the objects according to the invention in a particular manner. Titanium dioxide can be in rutile or anatase form or in amorphous form, but preferably in rutile and/or anatase form here. The preferred primary particle size is in the range from 5 to 50 nm. The primary particles here, in particular in the case of anatase, are preferably round, while rutile primary particles frequently occur in needle or spindle form right up to ovals ("egg-shaped"). However, round rutile primary particles can also be employed in accordance with the invention. Furthermore, in a variant of the invention, mixtures of rutile and anatase can be employed.

Particulate metal oxide which is suitable for the coating according to the invention can be obtained by various methods which are well known to the person skilled in the art. For example, the preparation can be carried out via a pyrogenic process (such as, for example, by means of flame pyrolysis), by means of a sol-gel process, a plasma process, by a hydrothermal process or by a combination of the various process variants.

The metal oxide, in particular if it is titanium dioxide, may also be doped. For the purposes of the present invention, doping is taken to mean the presence of corresponding ions in small amounts as flaws in the crystal lattice of the metal oxide.

Preferred dopings here are those with iron or cerium ions. Very particular preference is given to doping of the metal oxide with iron ions.

In a variant of the invention, it may also be preferred for the metal oxide to be doped with manganese ions.

In a further variant of the invention, however, it is preferred for the metal oxide not to be doped with manganese ions. It may even be preferred in accordance with the invention for the metal oxide not to be doped at all.

The manganese-containing coating should cover the particulate metal oxide as completely as possible. However, since the coating is inert as UV filter, it is preferred in accordance with the invention for the amount of coating to be kept small. It has been found that it is advantageous for the entire coating of the metal oxide to make up 5% by weight to 50% by weight, preferably 8% by weight to 30% by weight and particularly preferably 12% by weight to 20% by weight, based on the entire particulate UV protection agent.

The proportion of the manganese-containing layer is 0.1% by weight to 1% by weight, preferably 0.2% by weight to 0.7% by weight and particularly preferably 0.2% by weight or 0.5% by weight, based on the entire particulate UV protection agent.

It may be preferred here for the metal oxide parent substance to carry a first coating essentially consisting of manganese compounds and a second coating essentially consisting of aluminium and/or silicon compounds. In another variant of the invention, the metal oxide parent substance carries a first coating essentially consisting of aluminium and/or silicon compounds and a second coating essentially consisting of manganese compounds. It may likewise be preferred in accordance with the invention for the metal oxide parent substance to carry a coating essentially consisting of or consisting of a mixture of manganese compounds with aluminium and/or silicon compounds. In a preferred variant of the invention, the metal oxide parent substance carries a first coating consisting of aluminium oxide compounds and a second coating essentially consisting of or consisting of manganese compounds.

For the production of the manganese-containing coating, the manganese compound(s) employed is (are) preferably selected from the oxides, hydroxides, phosphates, sulfates and fatty acid salts of manganese, where the manganese coating is preferably manganese oxide.

The other coatings can be produced by methods known from the prior art. Corresponding generally applicable coating methods are indicated by way of example in the example part. The further coatings are preferably oxidic coatings of aluminium or silicon.

It may furthermore be preferred in accordance with the invention for the particulate UV protection agent to be aftertreated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

It may furthermore be preferred in accordance with the invention for the particulate UV protection agent to be hydrophobicised by conventional methods. Hydrophobicisation is carried out, for example, by application of a further organic coating or layer, as described, for example, in WO 2007/065574. The organic outer coating or layer can consist, for example, of silicone oils, alkylsilanes, olefinic acids, polyols or organophosphonic acids, or mixtures thereof. Illustrative hydrophobicisation components are Semimethicone, Methicone, Dimethicone/Methicone Copolymer, Trimethoxy-caprylsilane, Dimethicone (=Triethoxy-caprylsilane), Diphenyl Capryl Methicone, Alkyl Silane, Silicone, Polymethylmethacrylate dimethicone, long-chain organic acids, for example stearic acid, lauric acid, Cyclomethicone, lecithin, Cyclopentasiloxane, Cyclohexasiloxane, Hydroxystearic acid, Hydrogenated Polydecene, Polyhydroxystearic acid, Squalene, Octyl Silane (=Trimethoxy-caprylsilane), Cetearyl Alcohol, Cetyl PEG/PPG-10/1 Dimethicone, Dimethicone and PVP/Hexadecene Copolymer, Methicone and PVP/Hexadecene Copolymer, Sodium Hexamethylphosphate, PVP (=polyvinylpyrrolidone), Glyceryl Caprylate/Caprate, beeswax, synthetic waxes, microwaxes, Isopropyl Titanium Triisostearate/Triethoxycaprylsilane, Isopropyl Titanium Triisostearate/Dimethicone Crosspolymer, Magnesium Myristate, PEG-10 Dimethicone and Methicone, Poly-Acrylate/Methacrylate and copolymers, Polyglyceryl-3 Diisostearate, Cetyl Dimethicone Copolyol [the names are standardised, i.e. they are INCI names, which are defined in English]. Preference is given to an outer coating or layer comprising Semimethicone, Methicone, Dimethicone, Polysilicon-15, stearic acid, Glycerin or mixtures thereof. It would be particularly preferred to use Semimethicone, Dimethicone or Stearic acid, very particularly preferably Semimethicone.

The resultant particulate UV protection agent usually exhibits a particle size, determined by the Scherrer method, in the range from 5 nm to 100 nm, preferably in the range 8 to 50 nm and particularly preferably below 25 nm. The dimensions of the particulate UV protection agent, which can be determined in a transmission electron microscope, are usually a length of 10 to 160 nm and a width of 5 to 70 nm. The length is preferably in the range from 30 to 70 nm and the width in the range from 7 to 40 nm.

The particulate UV protection agent according to the invention exhibits advantageous properties here compared with the prior art, preferably with respect to:
- UV absorption, in particular broad-band or UV-B absorption,
- transparency in visible light (VIS),
- good, in particular increased photostability,
- reduced or inhibited photoactivity,
- antioxidant and/or free-radical-scavenging properties,
- hydrophilic surface, good incorporation and settling stability in aqueous phases,
- ready dispersibility in aqueous and oily phases and in particular a fine distribution in the dispersion,
- in particular in the case of an agent having a silicon dioxide coating which is preferred in accordance with the invention,
    - in combination with dibenzoylmethane derivatives, in particular:
        - no or reduced crystallisation of complexes of the dibenzoylmethane derivatives and/or
        - increased storage stability of the dibenzoylmethane derivatives and/or
        - improved light-protection action, in particular after storage,
    - in combination with self-tanning agents, in particular dihydroxyacetone, reduced destabilisation of the self-tanning agent compared with the prior art, or none at all, is observed,
    - in combination with benzophenone derivatives, in particular 2-hydroxy-4-methoxybenzophenone, stabilisation of the benzophenone derivatives is observed, in combination with cinnamic acid derivatives, such as ethylhexyl methoxycinnamate, stabilisation of the cinnamic acid derivatives is observed.

Furthermore, an emulsion comprising UV protection agents according to the invention typically has a slight tint. The white film on the skin, which is known from the application of titanium dioxide-containing suncreams and which can in some cases only be distributed until colourless with difficulty, attains a skin-like hue with the UV protection agent according to the invention. The use of the product is thus more comfortable for customers.

It has been found here, in particular, that it may be advantageous, for simultaneous realisation of the above-mentioned advantages, if the particulate metal oxide is doped with cerium or iron, preferably iron.

In another, likewise preferred variant of the present invention, however, the particulate metal oxide is free from dopants.

In a further embodiment, preference is given to a particulate UV protection agent, as described above, whose outer layer is a hydrophobicising layer.

As already mentioned above, the particulate UV protection agents having the properties according to the invention are obtained, for example, if a certain preparation process is observed.

Correspondingly, the present invention furthermore relates to a process for the preparation of a particulate metal oxide having light-protection properties which is characterised in that
a) a particulate metal oxide is subjected to hydrothermal treatment and
b) a manganese-containing coating is subsequently applied.

As already stated above, it may be preferred in this process for the particulate metal oxide employed in step a) to be a particulate titanium dioxide, which may preferably be doped with iron.

The hydrothermal treatment here is preferably carried out at temperatures in the range from 40 to 360° C., preferably in the range from 80 to 220° C. and particularly preferably in the range from 140 to 200° C. In a preferred process, subsequent heat treatment is omitted.

The hydrothermal treatment results in the formation of stable nanocrystallites of uniform size and shape. At low temperatures, "needle-shaped" crystallites form. With increasing temperature, the crystallites become rounded. Oval shapes form which become round particles at very high temperatures. In addition, uniform crystal growth occurs, which results in a reduction in the reactivity and photoactivity.

Advantages of the hydrothermal treatment compared with a conventional thermal treatment (heat treatment of a dried powder) are:
formation of uniform crystallite sizes with a narrow particle-size distribution
prevention of sintering effects (formation of undesired aggregates)

The coating in step b) is preferably carried out as a sol-gel process, in which a manganese sulfate solution, optionally together with further precursors, is particularly preferably added to a suspension of the metal oxide.

In an advantageous variant of the present invention, the sol-gel process is carried out at constant pH. The constant pH can be in a range from pH 2 to pH 11, with the pH preferably being in the range from pH=5 to pH=8, particularly preferably in the range from pH=6 to pH=7.

A further advantageous variant of the present invention is addition of all of the water-glass necessary for the aftertreatment at a pH=7 to pH=11 without keeping the pH constant. The pH is subsequently lowered to a value of pH=5 to pH=8, preferably to pH=6 to pH=7.

It is furthermore preferred for step b) to be carried out at elevated temperature, preferably at a temperature in the range from 50° C. to 100° C.

In all the said variants of the process according to the invention, a maturing time after the coating is complete is advantageous. The maturing time should be between 1 h and 8 h, preferably 2 h to 4 h, and should be carried out at a temperature of 50° C. to 110° C.

It may furthermore be advantageous with respect to the agglomerate sizes desired during later processing for the product subsequently to be ground. The conventional grinding techniques which can be used for particulate materials can be employed here.

In a preferred embodiment of the process, as described above, a hydrophobicising layer is applied in an aftertreatment step.

Further preferred combinations of embodiments are disclosed in the claims.

The invention furthermore relates to aqueous or oily dispersions comprising the particulate UV protection agents according to the invention. The dispersions can be prepared by conventional methods, as known to the person skilled in the art. Aqueous dispersions preferably comprise the particulate UV protection agent according to the invention, as described above, water and corresponding dispersion assistants.

Oily dispersions preferably comprise the particulate UV protection agent according to the invention, as described above, at least one cosmetic oil and corresponding dispersion assistants.

The compositions or dispersions may include or comprise, essentially consist of or consist of the said necessary or optional constituents.

Owing to the above-mentioned advantages, the present invention furthermore relates to a composition having light-protection properties which comprises at least one particulate UV protection agent according to the invention.

In a variant of the invention, the compositions are preferably compositions which can be applied topically, for example cosmetic or dermatological formulations. The compositions in this case comprise a cosmetically or dermatologically suitable vehicle and, depending on the desired property profile, optionally further suitable ingredients.

Further compositions which are preferred in accordance with the invention are selected from the group of fibres, textiles, including coatings thereof, paints, coating systems, films and packaging for the protection of foods, plants or industrial products.

Accordingly, the present invention furthermore relates to the use of a particulate UV protection agent according to the invention or of a particulate UV protection agent prepared by a process according to the invention for incorporation into paints, coating systems, films, packaging, fibres, textiles and rubber or silicone rubber mouldings, such as tyres or insulators.

Besides the advantages already mentioned above, the use of the particulate UV protection agents according to the invention in compositions which are emulsions can, in particular, also contribute towards stabilisation of the emulsion. In general, this can reduce the use of emulsifiers or, in an individual case (Pickering emulsion), even obviate the use of emulsifiers entirely. Preference is therefore also given in accordance with the invention to emulsifier-free emulsions which comprise the particulate UV protection agents according to the invention.

In a variant of the invention, preferred compositions having light-protection properties comprise at least one dibenzoylmethane derivative. The dibenzoylmethane derivatives used for the purposes of the present invention are, as already indicated, products which are already well known per se and which are described, in particular, in the above-mentioned specifications FR-A-2 326 405, FR-A-2 440 933 and EP-A-0 114 607.

The dibenzoylmethane derivatives which can be used can be selected, in particular, from the dibenzoylmethane derivatives of the following formula:

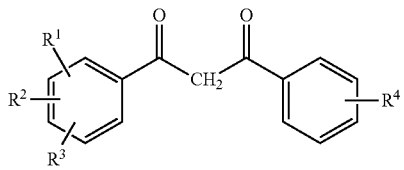

in which $R^1$, $R^2$, $R^3$ and $R^4$, which are identical or different from one another, denote hydrogen, a straight-chain or branched $C_{1-8}$-alkyl group or a straight-chain or branched $C_{1-8}$-alkoxy group. In accordance with the present invention, it is of course possible to use one dibenzoylmethane derivative or a plurality of dibenzoylmethane derivatives. Of the dibenzoylmethane derivatives to which the present invention specifically relates, mention may be made, in particular, of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-methoxy-tert-butyldibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane
and
2,6-dimethyl-4-tert-butyl-4'-methoxydibenzoylmethane,
this list being non-restrictive.

Of the above-mentioned dibenzoylmethane derivatives, particular preference is given to 4,4'-methoxy-tert-butyldibenzoylmethane and especially 4,4'-methoxy-tert-butyldibenzoylmethane, which is commercially available from Merck under the trade name Eusolex® 9020, this filter conforming to the following structural formula:

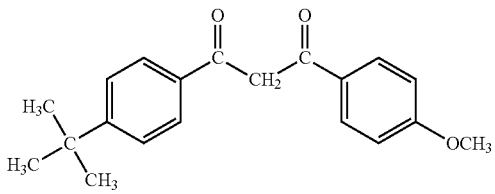 [SMILES: COc1ccc(C(=O)CC(=O)c2ccc(C(C)(C)C)cc2)cc1]

A further preferred dibenzoylmethane derivative is 4-isopropyldibenzoylmethane.

Further preferred compositions having light-protection properties comprise at least one benzophenone or benzophenone derivative, such as, particularly preferably, 2-hydroxy-4-methoxybenzophenone (for example Eusolex® 4360) or 2-hydroxy-4-methoxybenzophenone-5-sulfonic acid and the sodium salt thereof (for example Uvinul® MS-40).

The dibenzoylmethane derivative(s) or the benzophenone derivative(s) may be present in the compositions according to the invention in proportions which are generally in the range from 0.1% by weight to 10% by weight and preferably in proportions which are in the range from 0.3% by weight to 5% by weight, where these proportions are based on the total weight of the composition.

Owing to the above-mentioned advantages, the present invention may furthermore also relate to the use of a particulate metal oxide having light-protection properties according to the invention for the stabilisation of UV filters, in particular dibenzoylmethane and dibenzoylmethane derivatives or benzophenone and benzophenone derivatives.

In a further, likewise preferred embodiment of the present invention, the composition according to the invention comprises at least one self-tanning agent.

Advantageous self-tanning agents which can be employed are, inter alia:

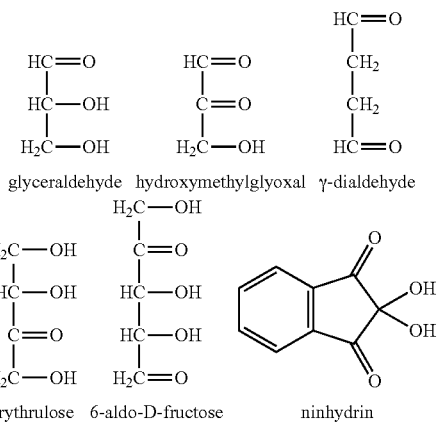

Mention should also be made of 5-hydroxy-1,4-naphthoquinone (juglone), which is extracted from the shells of fresh walnuts

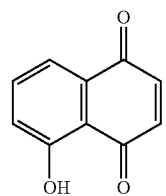

5-hydroxy-1,4-naphthoquinone (juglone)
and 2-hydroxy-1,4-naphthoquinone (lawsone), which occurs in henna leaves,

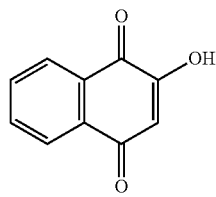 [SMILES: O=C1C=C(O)C(=O)c2ccccc21]

2-hydroxy-1,4-naphthoquinone (lawsone).

Very particular preference is given to 1,3-dihydroxyacetone (DHA), a tri-functional sugar which occurs in the human body, and derivatives thereof

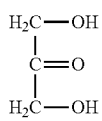

1,3-dihydroxyacetone (DHA).

The present invention furthermore relates to the use of a particulate UV protection agent according to the invention for the stabilisation of self-tanning agents, in particular dihydroxyacetone or dihydroxyacetone derivatives.

Furthermore, the compositions according to the invention may also comprise dyes and coloured pigments. The dyes and coloured pigments can be selected from the corresponding positive list in the German Cosmetics Regulation or the EC list of cosmetic colorants. In most cases, they are identical with the dyes approved for foods. Advantageous coloured pigments are, for example, titanium dioxide, mica, iron oxides (for example $Fe_2O_3$, $Fe_3O_4$, $FeO(OH)$) and/or tin oxide. Advantageous dyes are, for example, carmine, Berlin Blue, Chromium Oxide Green, Ultramarine Blue and/or Manganese Violet. It is particularly advantageous to select the dyes and/or coloured pigments from the following list. The Colour Index numbers (CINs) are taken from the Rowe Colour Index, 3rd Edition, Society of Dyers and Colourists, Bradford, England, 1971.

| Chemical or other name | CIN | Colour |
|---|---|---|
| Pigment Green | 10006 | Green |
| Acid Green 1 | 10020 | Green |
| 2,4-Dinitrohydroxynaphthalene-7-sulfonic acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-Dihydroxyazobenzene | 11920 | Orange |
| Solvent Red 3 | 12010 | Red |
| 1-(2'-Chloro-4'-nitro-1'-phenylazo)-2-hydroxynaphthalene | 12085 | Red |
| Pigment Red 3 | 12120 | Red |
| Ceres Red; Sudan Red; Fat Red G | 12150 | Red |
| Pigment Red 112 | 12370 | Red |
| Pigment Red 7 | 12420 | Red |
| Pigment Brown 1 | 12480 | Brown |
| 4-(2'-Methoxy-5'-sulfonyldiethylamido-1'-phenylazo)-3-hydroxy-5"-chloro-2",4"-dimethoxy-2-naphthanilide | 12490 | Red |
| Disperse Yellow 16 | 12700 | Yellow |
| 1-(4-Sulfo-1-phenylazo)-4-aminobenzene-5-sulfonic acid | 13015 | Yellow |
| 2,4-Dihydroxyazobenzene-4'-sulfonic acid | 14270 | Orange |
| 2-(2,4-Dimethylphenylazo-5-sulfonyl)-1-hydroxynaphthalene-4-sulfonic acid | 14700 | Red |
| 2-(4-Sulfo-1-naphthylazo)-1-naphthol-4-sulfonic acid | 14720 | Red |
| 2-(6-Sulfo-2,4-xylylazo)-1-naphthol-5-sulfonic acid | 14815 | Red |
| 1-(4'-Sulfophenylazo)-2-hydroxynaphthalene | 15510 | Orange |
| 1-(2-Sulfonyl-4-chloro-5-carboxy-1-phenylazo)-2-hydroxynaphthalene | 15525 | Red |
| 1-(3-Methylphenylazo-4-sulfonyl)-2-hydroxynaphthalene | 15580 | Red |
| 1-(4',(8')-Sulfonylnaphthylazo)-2-hydroxynaphthalene | 15620 | Red |
| 2-Hydroxy-1,2'-azonaphthalene-1'-sulfonic acid | 15630 | Red |
| 3-Hydroxy-4-phenylazo-2-naphthylcarboxylic acid | 15800 | Red |
| 1-(2-Sulfo-4-methyl-1-phenylazo)-2-naphthylcarboxylic acid | 15850 | Red |
| 1-(2-Sulfo-4-methyl-5-chloro-1-phenylazo)-2-hydroxynaphthalene-3-carboxylic acid | 15865 | Red |
| 1-(2-Sulfo-1-naphthylazo)-2-hydroxynaphthalene-3-carboxylic acid | 15880 | Red |
| 1-(3-Sulfo-1-phenylazo)-2-naphthol-6-sulfonic acid | 15980 | Orange |
| 1-(4-Sulfo-1-phenylazo)-2-naphthol-6-sulfonic acid | 15985 | Yellow |
| Allura Red | 16035 | Red |
| 1-(4-Sulfo-1-naphthylazo)-2-naphthol-3,6-disulfonic acid | 16185 | Red |
| Acid Orange 10 | 16230 | Orange |
| 1-(4-Sulfo-1-naphthylazo)-2-naphthol-6,8-disulfonic acid | 16255 | Red |
| 1-(4-Sulfo-1-naphthylazo)-2-naphthol-3,6,8-trisulfonic acid | 16290 | Red |
| 8-Amino-2-phenylazo-1-naphthol-3,6-disulfonic acid | 17200 | Red |
| Acid Red 1 | 18050 | Red |
| Acid Red 155 | 18130 | Red |
| Acid Yellow 121 | 18690 | Yellow |
| Acid Red 180 | 18736 | Red |
| Acid Yellow 11 | 18820 | Yellow |
| Acid Yellow 17 | 18965 | Yellow |
| 4-(4-Sulfo-1-phenylazo)-1-(4-sulfophenyl)-5-hydroxy-pyrazolone-3-carboxylic acid | 19140 | Yellow |
| Pigment Yellow 16 | 20040 | Yellow |
| 2,6-(4'-Sulfo-2",4"-dimethyl)bisphenylazo)-1,3-dihydroxybenzene | 20170 | Orange |
| Acid Black 1 | 20470 | Black |
| Pigment Yellow 13 | 21100 | Yellow |
| Pigment Yellow 83 | 21108 | Yellow |
| Solvent Yellow | 21230 | Yellow |
| Acid Red 163 | 24790 | Red |
| Acid Red 73 | 27290 | Red |

-continued

| Chemical or other name | CIN | Colour |
|---|---|---|
| 2-[4'-(4''-Sulfo-1''-phenylazo)-7'-sulfo-1'-naphthylazo]-1-hydroxy-7-aminonaphthalene-3,6-disulfonic acid | 27755 | Black |
| 4-[4''-Sulfo-1''-phenylazo)-7'-sulfo-1'-naphthylazo]-1-hydroxy-8-acetylaminonaphthalene-3,5-disulfonic acid | 28440 | Black |
| Direct Orange 34, 39, 44, 46, 60 | 40215 | Orange |
| Food Yellow | 40800 | Orange |
| trans-β-Apo-8'-carotene aldehyde ($C_{30}$) | 40820 | Orange |
| trans-Apo-8'-carotinic acid ($C_{30}$) ethyl ester | 40850 | Orange |
| Canthaxanthine | 40850 | Orange |
| Acid Blue 1 | 42045 | Blue |
| 2,4-Disulfo-5-hydroxy-4'-4''-bis(diethylamino)triphenylcarbinol | 42051 | Blue |
| 4-[(4-N-Ethyl-p-sulfobenzylamino)phenyl-(4-hydroxy-2-sulfophenyl)(methylene)-1-(N-ethyl-N-p-sulfobenzyl)-2,5-cyclohexadienimine] | 42053 | Green |
| Acid Blue 7 | 42080 | Blue |
| (N-Ethyl-p-sulfobenzylamino)phenyl-(2-sulfophenyl)-methylene-(N-ethyl-N-p-sulfobenzyl)-$\Delta^{2,5}$-cyclohexadienimine | 42090 | Blue |
| Acid Green 9 | 42100 | Green |
| Diethyldisulfobenzyldi-4-amino-2-chlorodi-2-methyl-fuchsonimmonium | 42170 | Green |
| Basic Violet 14 | 42510 | Violet |
| Basic Violet 2 | 42520 | Violet |
| 2'-Methyl-4'-(N-ethyl-N-m-sulfobenzyl)amino-4''-(N-diethyl)amino-2-methyl-N-ethyl-N-m-sulfobenzyl-fuchsonimmonium | 42735 | Blue |
| 4'-(N-Dimethyl)amino-4''-(N-phenyl)aminonaphtho-N-dimethylfuchsonimmonium | 44045 | Blue |
| 2-Hydroxy-3,6-disulfo-4,4'-bisdimethylaminonaphtho-fuchsonimmonium | 44090 | Green |
| Acid Red 52 | 45100 | Red |
| 3-(2'-Methylphenylamino)-6-(2'-methyl-4'-sulfophenyl-amino)-9-(2''-carboxyphenyl)xanthenium salt | 45190 | Violet |
| Acid Red 50 | 45220 | Red |
| Phenyl-2-oxyfluorone-2-carboxylic acid | 45350 | Yellow |
| 4,5-Dibromofluorescein | 45370 | Orange |
| 2,4,5,7-Tetrabromofluorescein | 45380 | Red |
| Solvent Dye | 45396 | Orange |
| Acid Red 98 | 45405 | Red |
| 3',4',5',6'-Tetrachloro-2,4,5,7-tetrabromofluorescein | 45410 | Red |
| 4,5-Diiodofluorescein | 45425 | Red |
| 2,4,5,7-Tetraiodofluorescein | 45430 | Red |
| Quinophthalone | 47000 | Yellow |
| Quinophthalonedisulfonic acid | 47005 | Yellow |
| Acid Violet 50 | 50325 | Violet |
| Acid Black 2 | 50420 | Black |
| Pigment Violet 23 | 51319 | Violet |
| 1,2-Dioxyanthraquinone, calcium-aluminium complex | 58000 | Red |
| 3-Oxypyrene-5,8,10-sulfonic acid | 59040 | Green |
| 1-Hydroxy-4-N-phenylaminoanthraquinone | 60724 | Violet |
| 1-Hydroxy-4-(4'-methylphenylamino)anthraquinone | 60725 | Violet |
| Acid Violet 23 | 60730 | Violet |
| 1,4-Di(4'-methylphenylamino)anthraquinone | 61565 | Green |
| 1,4-Bis(o-sulfo-p-toluidino)anthraquinone | 61570 | Green |
| Acid Blue 80 | 61585 | Blue |
| Acid Blue 62 | 62045 | Blue |
| N,N'-Dihydro-1,2,1',2'-anthraquinonazine | 69800 | Blue |
| Vat Blue 6; Pigment Blue 64 | 69825 | Blue |
| Vat Orange 7 | 71105 | Orange |
| Indigo | 73000 | Blue |
| Indigodisulfonic acid | 73015 | Blue |
| 4,4'-Dimethyl-6,6'-dichlorothioindigo | 73360 | Red |
| 5,5'-Dichloro-7,7'-dimethylthioindigo | 73385 | Violet |
| Quinacridone Violet 19 | 73900 | Violet |
| Pigment Red 122 | 73915 | Red |
| Pigment Blue 16 | 74100 | Blue |
| Phthalocyanine | 74160 | Blue |
| Direct Blue 86 | 74180 | Blue |
| Chlorinated phthalocyanine | 74260 | Green |
| Natural Yellow 6, 19; Natural Red 1 | 75100 | Yellow |
| Bixin, Nor-Bixin | 75120 | Orange |
| Lycopene | 75125 | Yellow |
| trans-alpha-, -beta- or -gamma-Carotene | 75130 | Orange |
| Keto and/or hydroxyl derivatives of carotene | 75135 | Yellow |
| Guanine or pearlescent agent | 75170 | White |
| 1,7-Bis(4-hydroxy-3-methoxyphenyl)-1,6-heptadiene-3,5-dione | 75300 | Yellow |
| Complex salt (Na, Al, Ca) of carminic acid | 75470 | Red |

-continued

| Chemical or other name | CIN | Colour |
|---|---|---|
| Chlorophyll a and b; copper compounds of chlorophylls and chlorophyllines | 75810 | Green |
| Aluminium | 77000 | White |
| Aluminium hydroxide | 77002 | White |
| Water-containing aluminium silicates | 77004 | White |
| Ultramarine | 77007 | Blue |
| Pigment Red 101 and 102 | 77015 | Red |
| Barium sulfate | 77120 | White |
| Bismuth oxychloride and mixtures thereof with mica | 77163 | White |
| Calcium carbonate | 77220 | White |
| Calcium sulfate | 77231 | White |
| Carbon | 77266 | Black |
| Pigment Black 9 | 77267 | Black |
| Carbo medicinalis vegetabilis | 77268:1 | Black |
| Chromium oxide | 77288 | Green |
| Chromium oxide, water-containing | 77278 | Green |
| Pigment Blue 28, Pigment Green 14 | 77346 | Green |
| Pigment Metal 2 | 77400 | Brown |
| Gold | 77480 | Brown |
| Iron oxides and hydroxides | 77489 | Orange |
| Iron oxide | 77491 | Red |
| Iron oxide hydrate | 77492 | Yellow |
| Iron oxide | 77499 | Black |
| Mixtures of iron(II) and iron(III) hexacyanoferrate | 77510 | Blue |
| Pigment White 18 | 77713 | White |
| Manganese ammonium diphosphate | 77742 | Violet |
| Manganese phosphate; $Mn_3(PO_4)_2 \cdot 7\ H_2O$ | 77745 | Red |
| Silver | 77820 | White |
| Titanium dioxide and mixtures thereof with mica | 77891 | White |
| Zinc oxide | 77947 | White |
| 6,7-Dimethyl-9-(1'-D-ribityl)isoalloxazine, lactoflavin | | Yellow |
| Sugar dye | | Brown |
| Capsanthin, capsorubin | | Orange |
| Betanin | | Red |
| Benzopyrylium salts, anthocyans | | Red |
| Aluminium, zinc, magnesium and calcium stearate | | White |
| Bromothymol Blue | | Blue |

It may furthermore be favourable to select, as dye, one or more substances from the following group:
2,4-dihydroxyazobenzene, 1-(2'-chloro-4'-nitro-1'-phenylazo)-2-hydroxynaphthalene, Ceres Red, 2-(4-sulfo-1-naphthylazo)-1-naphthol-4-sulfonic acid, the calcium salt of 2-hydroxy-1,2'-azonaphthalene-1'-sulfonic acid, the calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-naphthylazo)-2-naphthol-3,6-disulfonic acid, 1-(4-sulfo-1-naphthylazo)-2-naphthol-6,8-disulfonic acid, the aluminium salt of 4-(4-sulfo-1-phenylazo)-2-(4-sulfophenyl)-5-hydroxypyrazolone-3-carboxylic acid, the aluminium and zirconium salts of 4,5-dibromofluorescein, the aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium salt of indigodisulfonic acid, red and black iron oxide (CIN: 77 491 (red) and 77 499 (black)), iron oxide hydrate (CIN: 77492), manganese ammonium diphosphate and titanium dioxide.

Also advantageous are oil-soluble natural dyes, such as, for example, paprika extract, β-carotene or cochineal, in particular β-carotene.

Also advantageous for the purposes of the present invention are gel creams comprising pearlescent pigments. Particular preference is given to the types of pearlescent pigment listed below:

1. Natural pearlescent pigments, such as, for example,
   "pearl essence" (guanine/hypoxanthine mixed crystals from fish scales) and
   "mother-of-pearl" (ground mussel shells)
2. Monocrystalline pearlescent pigments, such as, for example, bismuth oxychloride (BiOCl)
3. Layered substrate pigments: for example mica/metal oxide The basis for pearlescent pigments is formed by, for example, pulverulent pigments or castor oil dispersions of bismuth oxychloride and/or titanium dioxide as well as bismuth oxychloride and/or titanium dioxide on mica.

The lustre pigment listed under CIN 77163, for example, is particularly advantageous.

Also advantageous are, for example, the following pearlescent pigment types based on mica/metal oxide:

| Group | Coating/layer thickness | Colour |
|---|---|---|
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Coloured lustre pigments | $Fe_2O_3$ | bronze |
| | $Fe_2O_3$ | copper |
| | $Fe_2O_3$ | red |
| | $Fe_2O_3$ | red-violet |
| | $Fe_2O_3$ | red-green |
| | $Fe_2O_3$ | black |

| Group | Coating/layer thickness | Colour |
|---|---|---|
| Combination pigments | TiO$_2$/Fe$_2$O$_3$ | gold shades |
| | TiO$_2$/Cr$_2$O$_3$ | green |
| | TiO$_2$/Berlin Blue | dark blue |

Particular preference is given, for example, to the pearlescent pigments available from Merck under the trade names Timiron, Colorona or Dichrona.

The list of the said pearlescent pigments is of course not intended to be limiting. Pearlescent pigments which are advantageous for the purposes of the present invention can be obtained by numerous routes known per se. For example, other substrates apart from mica can also be coated with further metal oxides, such as, for example, silica and the like. For example, TiO$_2$- and Fe$_2$O$_3$-coated SiO$_2$ particles ("Ronasphere" grades), which are marketed by Merck and are particularly suitable for the optical reduction of fine wrinkles, are advantageous.

It may additionally be advantageous to completely omit a substrate such as mica. Particular preference is given to pearlescent pigments prepared using SiO$_2$. Such pigments, which may additionally also have goniochromatic effects, are available, for example, from BASF under the trade name Sicopearl Fantastico.

It may also be advantageous to employ Engelhard/Mearl pigments based on calcium sodium borosilicate coated with titanium dioxide. These are available under the name Reflecks. Due to their particle size of 40-80 µm, they have a glitter effect in addition to the colour.

Also particularly advantageous are effect pigments available from Flora Tech under the trade name Metasomes Standard/Glitter in various colours (yellow, red, green, blue). The glitter particles here are in the form of mixtures with various assistants and dyes (such as, for example, the dyes with the Colour Index (CI) numbers 19140, 77007, 77289, 77491).

The dyes and pigments can be in individual form or in the form of a mixture and mutually coated with one another, with different colour effects generally being caused by different coating thicknesses. The total amount of dyes and colouring pigments is advantageously selected from the range from, for example, 0.1% by weight to 30% by weight, preferably from 0.5 to 15% by weight, in particular from 1.0 to 10% by weight, in each case based on the total weight of the compositions.

In accordance with the invention, the particulate UV protection agents may preferably also be provided with a surface treatment which strengthens the hydrophilic or hydrophobic properties. Suitable for hydrophobic modification is, for example, a silicone or silane coating.

The silicones are, as is known, organosilicon polymers or oligomers having a straight-chain or cyclic, branched or crosslinked structure with various molecular weights which are obtained by polymerisation and/or polycondensation of suitably functionalised silanes and are essentially formed from recurring main units in which the silicon atoms are linked to one another via oxygen atoms (siloxane bond), where optionally substituted hydrocarbon groups are bonded directly to the silicon atoms via a carbon atom. The commonest hydrocarbon groups are the alkyl groups and in particular methyl, the fluoroalkyl groups, the aryl groups and in particular phenyl, and the alkenyl groups and in particular vinyl. Further types of group which can be bonded to the siloxane chain either directly or via a hydrocarbon group are, in particular, hydrogen, the halogens and in particular chlorine, bromine or fluorine, the thiols, the alkoxy groups, the polyoxyalkylene groups (or polyethers) and in particular polyoxyethylene and/or polyoxypropylene, hydroxyl groups or hydroxyalkyl groups, the optionally substituted amino groups, the amide groups, the acyloxy groups or acyloxyalkyl groups, the hydroxyalkylamino groups or aminoalkyl groups, quaternary ammonium groups, amphoteric groups or betaine groups, anionic groups, such as carboxylates, thioglycolates, sulfosuccinates, thiosulfates, phosphates and sulfates, where this list is of course in no way limiting (so-called 'organomodified' silicones).

For the purposes of the present invention, the term 'silicones' is also intended to encompass and cover the silanes and in particular the alkylsilanes required for their preparation.

The silicones which are suitable for the present invention and can be used for sheathing the particulate UV protection agents are preferably selected from the alkylsilanes, the polydialkylsiloxanes and the polyalkylhydrogenosiloxanes. The silicones are more preferably selected from octyltrimethylsilane, the polydimethylsiloxanes and the polymethylhydrogenosiloxanes.

The particulate UV protection agents may be present in the compositions according to the invention in proportions which are generally in the range from 0.01 to 50% by weight and preferably in proportions in the range from 0.5 to 20% by weight, where these proportions are based on the total weight of the composition.

Furthermore, combinations with further particulate UV filters, both as powder and also as dispersion or paste, of the following types are also possible.

Preference is given here both to those from the group of the titanium dioxides, such as, for example, coated titanium dioxide (for example Eusolex® T-2000, Eusolex®T-AQUA, Eusolex®T-AVO, Eusolex®T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments is greater than or equal to 200 nm, for example Hombitec® COS.

It may furthermore be preferred in accordance with the invention for the compositions to comprise inorganic UV filters which have been aftertreated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

Further particulate UV filters which are preferably employed here are:
  untreated titanium dioxides, such as, for example, the products Microtitanium Dioxide MT 500 B from Tayca; titanium dioxide P25 from Degussa,
  aftertreated micronised titanium dioxides with aluminium oxide and silicon dioxide aftertreatment, such as, for example, the product "Microtitanium Dioxide MT 100 SA" from Tayca; or the product "Tioveil Fin" from Uniqema,
  aftertreated micronised titanium dioxides with aluminium oxide and/or aluminium stearate/laurate aftertreatment, such as, for example, Microtitanium Dioxide MT 100 T from Tayca, Eusolex T-2000 from Merck, aftertreated micronised titanium dioxides with iron oxide and/or iron stearate aftertreatment, such as, for example, the product "Microtitanium Dioxide MT 100 F" from Tayca, aftertreated micronised titanium dioxides with silicon dioxide, aluminium oxide and silicone aftertreatment, such as, for example, the product "Microtitanium Dioxide MT 100 SAS" from Tayca, aftertreated micronised titanium dioxides with sodium hexametaphosphates, such as, for example, the product "Microtitanium Dioxide MT 150 W" from Tayca.

The treated micronised titanium dioxides employed for the combination may also be aftertreated with:

octyltrimethoxysilanes; such as, for example, the product Tego Sun T 805 from Degussa, silicon dioxide; such as, for example, the product Parsol T-X from DSM, aluminium oxide and stearic acid; such as, for example, the product UV-Titan M160 from Kemira, aluminium and glycerin; such as, for example, the product UV-Titan from Kemira, aluminium and silicone oils, such as, for example, the product UV-Titan M262 from Kemira, sodium hexametaphosphate and polyvinylpyrrolidone, polydimethylsiloxanes, such as, for example, the product 70250 Cardre UF TiO2Sl3 from Cardre, polydimethylhydrogenosiloxanes, such as, for example, the product Microtitanium Dioxide USP Grade Hydrophobic from Color Techniques.

The combination with the following products may furthermore also be advantageous:

untreated zinc oxides, such as, for example, the product Z-Cote from BASF (Sunsmart), Nanox from Elementis aftertreated zinc oxides, such as, for example, the following products:

"Zinc Oxide CS-5" from Toshibi (ZnO aftertreated with polymethylhydrogenosiloxanes)

Nanogard Zinc Oxide FN from Nanophase Technologies

"SPD-Z1" from Shin-Etsu (ZnO aftertreated with a silicone-grafted acrylic polymer, dispersed in cyclodimethylsiloxanes)

"Escalol Z100" from ISP (aluminium oxide-aftertreated ZnO dispersed in an ethylhexyl methoxycinnamate/PVP-hexadecene/-methicone copolymer mixture)

"Fuji ZNO-SMS-10" from Fuji Pigment (ZnO aftertreated with silicon dioxide and polymethylsilesquioxane)

untreated cerium oxide micropigment, for example with the name "Colloidal Cerium Oxide" from Rhone Poulenc untreated and/or aftertreated iron oxides with the name Nanogar from Arnaud.

For example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide, zinc oxide mixtures, such as, for example, the product UV-Titan M261 from Kemira, in combination with the UV protection agent according to the invention.

These inorganic UV filters are generally incorporated into cosmetic compositions in an amount of 0.1 to 25 percent by weight, preferably 2-10%. In particular, it may be preferred here for a nanoparticulate UV protection agent according to the invention to be present in one phase in emulsions and a further inorganic UV filter to be present in the other phase.

The sunscreens according to the invention may of course comprise one or more additional hydrophilic or lipophilic sun-protection filter(s) which is (are) effective in the UV-A region and/or UV-B region and/or IR and/or VIS region (absorbers). These additional filters can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO 93/04665. Further examples of organic filters are indicated in the patent application EP-A 0 487 404. The said UV filters are usually named below in accordance with INCI nomenclature.

Particular mention should be made here of:

para-aminobenzoic acid and derivatives thereof: PABA, Ethyl PABA, Ethyl dihydroxypropyl PABA, Ethylhexyl dimethyl PABA, for example marketed under the name "Escalol 507" by ISP, Glyceryl PABA, PEG-25 PABA, for example marketed under the name "Uvinul P25" by BASF.

Salicylates: homosalate marketed under the name "Eusolex HMS" by Merck; ethylhexyl salicylate, for example marketed under the name "Neo Heliopan OS" by Haarmann and Reimer, dipropylene glycol salicylate, for example marketed under the name "Dipsal" by Scher, TEA salicylate, for example marketed under the name "Neo Heliopan TS" by Haarmann and Reimer.

β,β-Diphenylacrylate derivatives: octocrylene, for example marketed under the name "Uvinul N539" by BASF, etocrylene, for example marketed under the name "Uvinul N35" by BASF.

Benzophenone derivatives: benzophenone-1, for example marketed under the name "Uvinul 400"; benzophenone-2, for example marketed under the name "Uvinul D50"; benzophenone-3 or oxybenzone, for example marketed under the name "Uvinul M40"; benzophenone-4, for example marketed under the name "Uvinul MS40"; benzophenone-9, for example marketed under the name "Uvinul DS-49" by BASF, benzophenone-5, benzophenone-6, for example marketed under the name "Helisorb 11" by Norquay, benzophenone-8, for example marketed under the name "Spectra-Sorb UV-24" by American Cyanamid, benzophenone-12 n-hexyl 2-(4-diethylamino-2-hydroxybenzoyl)benzoate.

Benzylidenecamphor derivatives: 3-benzylidenecamphor, for example marketed under the name "Mexoryl SD" by Chimex, 4-methylbenzylidenecamphor, for example marketed under the name "Eusolex 6300" by Merck, benzylidenecamphorsulfonic acid, for example marketed under the name "Mexoryl SL" by Chimex, camphor benzalkonium methosulfate, for example marketed under the name "Mexoryl SO" by Chimex, terephthalylidenedicamphorsulfonic acid, for example marketed under the name "Mexoryl SX" by Chimex, polyacrylamidomethylbenzylidenecamphor marketed under the name "Mexoryl SW" by Chimex.

Phenylbenzimidazole derivatives: phenylbenzimidazolesulfonic acid, for example marketed under the name "Eusolex 232" by Merck, disodium phenyl dibenzimidazole tetrasulfonate, for example marketed under the name "Neo Heliopan AP" by Haarmann and Reimer.

Phenylbenzotriazole derivatives: drometrizole trisiloxane, for example marketed under the name "Silatrizole" by Rhodia Chimie, methylenebis(benzotriazolyl)tetramethylbutylphenol in solid form, for example marketed under the name "MIXXIM BB/100" by Fairmount Chemical, or in micronised form as an aqueous dispersion, for example marketed under the name "Tinosorb M" by Ciba Specialty Chemicals.

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl-4'-aminobenzalmalonate)-s-triazine.

Anthraniline derivatives: menthyl anthranilate, for example marketed under the name "Neo Heliopan MA" by Haarmann and Reimer.

Imidazole derivatives: ethylhexyldimethoxybenzylidenedioxoimidazoline propionate.

Benzalmalonate derivatives: polyorganosiloxanes containing functional benzalmalonate groups, such as, for example, polysilicone-15, for example marketed under the name "Parsol SLX" by Hoffmann LaRoche.

4,4-Diarylbutadiene derivatives: 1,1-dicarboxy(2,2'-dimethylpropyl)-4,4-diphenylbutadiene.

Benzoxazole derivatives: 2,4-bis[5-(1-dimethylpropyl)benzoxazol-2-yl(4-phenyl)imino]-6-(2-ethylhexyl)imino-1,3,5-triazine, for example marketed under the name Uvasorb K2A by Sigma 3V, and mixtures comprising this.

The compounds listed should only be regarded as examples. It is of course also possible to use other UV filters. In particular, organic particulate UV filters, as described, for example, in the patent application WO 99/66896, can advantageously also be combined with the particulate UV protection agents according to the invention.

The organic UV-protecting substances which are suitable for combination with the UV protection agent according to the invention can preferably be selected from the following list: Ethylhexyl salicylate, Octocrylene, Butylmethoxydibenzoylmethane, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-Bis[5-(1-dimethylpropyl)benzoxazol-2-yl(4-phenyl)imino]-6-(2-ethylhexyl)imino-1,3,5-triazine and mixtures thereof.

These organic UV filters are generally incorporated into cosmetic formulations in an amount of 0.01 to 20 percent by weight, preferably 1-10% by weight.

Organic UV filters are generally incorporated into cosmetic formulations in a total amount of 0.01 to 20 percent by weight, preferably 0.5-20%.

Preferred compositions may also comprise compounds of the formula I

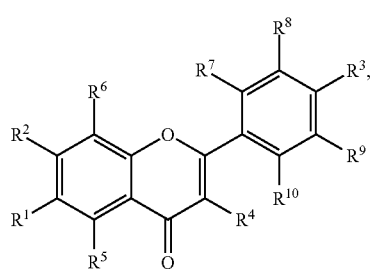

I where $R^1$ and $R^2$ are selected from
H
and $OR^{11}$, where $OR^{11}$, independently of one another, stands for
OH
straight-chain or branched $C_1$- to $C_{20}$-alkoxy groups,
straight-chain or branched $C_3$- to $C_{20}$-alkenyloxy groups,
straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or
$C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or
mono- and/or oligoglycosyl radicals,
with the proviso that at least one radical from $R^1$ and $R^2$ stands for $OR^{11}$, and $R^3$ stands for a radical $OR^{11}$ and
$R^4$ to $R^7$ and $R^{10}$ may be identical or different and, independently of one another, stand for
H
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3, and
$R^8$ and $R^9$ may be identical or different and, independently of one another, stand for
H
$OR^{11}$
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3.

Advantages of the compositions according to the invention are, in particular, the UV light-filtering action and the good skin tolerance. In addition, the compounds of the formula I described here are colourless or only weakly coloured and thus, in contrast to many known naturally occurring flavonoids, do not result in discoloration of the compositions.

The flavonoids of the formula I to be employed in accordance with the invention include broad-band UV filters, other likewise preferred compounds of the formula I exhibit an absorption maximum in the boundary region between UV-B and UV-A radiation. As UV-A-II filters, they therefore advantageously supplement the absorption spectrum of commercially available UV-B and UV-A-I filters. Preferred compositions having light-protection properties according to the invention comprise at least one compound of the formula I, where $R^3$ stands for
OH or
straight-chain or branched $C_1$- to $C_{20}$-alkoxy groups, preferably methoxy, ethoxy or ethylhexyloxy, or mono- and/or oligoglycosyl radicals, preferably glucosyl radicals, and $R^1$ and/or $R^2$ preferably stand for OH or straight-chain or branched $C_1$- to $C_{20}$-alkoxy groups, preferably methoxy, ethoxy or ethylhexyloxy, or mono- and/or oligoglycosyl radicals, preferably glucosyl radicals.

These preferred compounds are distinguished by particularly strong UV absorption.

In addition, preferred compounds of this type have advantages on incorporation into the compositions:

mono- and/or oligoglycosyl radicals improve the water solubility of the compounds to be employed in accordance with the invention;

straight-chain or branched $C_1$- to $C_{20}$-alkoxy groups, in particular the long-chain alkoxy functions, such as ethylhexyloxy groups, increase the oil solubility of the compounds;

i.e. the hydrophilicity or lipophilicity of the compounds of the formula I can be controlled via a suitable choice of the substituents. Preferred mono- or oligosaccharide radicals here are hexosyl radicals, in particular rhamnosyl radicals and glucosyl radicals. However, other hexosyl radicals, for example allosyl, altrosyl, galactosyl, gulosyl, idosyl, mannosyl and talosyl, may also, if desired, advantageously be used. It may also be advantageous to use pentosyl radicals. The glycosyl radicals can be bonded to the parent substance α- or β-glycosidically. A preferred disaccharide is, for example, 6-O-(6-deoxy-α-L-mannopyranosyl)-β-D-glucopyranoside.

It has been found that the intensity of the UV absorption is particularly high if $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy.

Particular preference is therefore given in accordance with the invention to compositions having light-protection properties comprising at least one compound of the formula I which is characterised in that $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy. It is particularly preferred here if $R^8$ and $R^9$ stand for H.

The compounds of the formula I are typically employed in accordance with the invention in amounts of 0.01 to 20% by weight, preferably in amounts of 0.5% by weight to 10% by weight and particularly preferably in amounts of 1 to 8% by weight. The person skilled in the art is presented with absolutely no difficulties at all in correspondingly selecting the amounts depending on the intended light protection factor of the composition.

Combination of one or more particulate UV protection agents with further UV filters enables the protective action against harmful effects of UV radiation to be optimised. Optimised compositions may comprise, for example, the combination of the organic UV filters 4'-methoxy-6-hydroxy-flavone with 1-(4-tert-butylphenyl)-3-(4-methoxyphenyl)propane-1,3-dione and 3-(4'-methylbenzylidene)-dl-camphor.

All the said UV filters, including the compounds of the formula I, can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables preparation problems caused by the interaction of individual composition constituents with one another, such as crystallisation processes, precipitation and agglomeration, to be avoided since the interaction is suppressed.

It may therefore be preferred in accordance with the invention for one or more of the compounds of the formula I or the above-mentioned UV filters to be in encapsulated form. It is advantageous here for the capsules to be so small that they cannot be observed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed in accordance with the invention have walls which can be obtained by a sol-gel process, as described in the applications WO 00/09652, WO 00/72806 and WO 00/71084. Preference is in turn given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

If the compositions according to the invention comprise compounds of the formula I containing free hydroxyl groups, they additionally, besides the properties described, exhibit an action as antioxidant and/or free-radical scavenger. Preference is therefore also given to compositions having light-protection properties comprising at least one compound of the formula I which is characterised in that at least one of the radicals $R^1$ to $R^3$ stands for OH, preferably with at least one of the radicals $R^1$ or $R^2$ standing for OH.

In general, the UV protection agents according to the invention act as antioxidant, in particular via their action as free-radical scavengers. Free radicals of this type are not generated only by sunlight, but instead are formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leukocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

It is assumed that UV protection agents according to the invention also act as enzyme inhibitors. They are thought to inhibit histidine decarboxylase, protein kinases, elastase, aldose reductase and hyaluronidase, and therefore enable the intactness of the basic substance of vascular sheaths to be maintained. Furthermore, they are thought to inhibit catechol O-methyl transferase non-specifically, causing the amount of available catecholamines and thus the vascular strength to be increased. Furthermore, they inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. The present invention also expressly relates to all these uses and to the use of the compounds of the formula I for the preparation of compositions which can be employed correspondingly.

The antioxidant action of the UV protection agents according to the invention can be investigated using various tests. Determination methods for the properties according to the invention are indicated in the example part, and can be used not only for the specific examples indicated there, but also very generally.

It is particularly preferred in accordance with the invention for the decadic absorption coefficient of a surface coating comprising the UV protection agent at 300 nm to be greater than 30, preferably greater than 35 and particularly preferably greater than 40. It may furthermore be preferred for the decadic absorption coefficient of a surface coating comprising the UV protection agent at 560 nm to be less than 1.

Compositions according to the invention may also be suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spino-cellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

The protective action against oxidative stress or against the effect of free radicals can be further improved if the compositions comprise one or more antioxidants.

In a preferred embodiment of the present invention, the composition is therefore a composition for the protection of body cells against oxidative stress, in particular for reducing skin ageing, characterised in that it preferably comprises one or more antioxidants.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbylpalmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin A palmitate, vitamin C, DL-α-tocopherol, tocopherol E acetate, nicotinic acid, pantothenic acid and biotin.

Besides the compounds described here, the compositions according to the invention may, in a particularly preferred variant, also comprise at least one compound conforming to the formula II as antioxidant

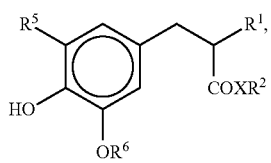

where
$R^1$ is selected from $-C(O)CH_3$, $-CO_2R^3$, $-C(O)NH_2$ and $-C(O)N(R^4)_2$;
X is O or NH;
$R^2$ stands for a linear or branched $C_{1-30}$-alkyl radical;
$R^3$ stands for a linear or branched $C_{1-20}$-alkyl radical;
all $R^4$, independently of one another, stand for H or linear or branched $C_{1-8}$-alkyl radicals;
$R^5$ stands for H, a linear or branched $C_{1-8}$-alkyl radical or a linear or branched $-O-C_{1-8}$-alkyl radical; and
$R^6$ stands for a $C_{1-8}$-alkyl radical.

The antioxidant of the formula II is particularly preferably di-2-ethylhexyl 4-hydroxy-3,5-dimethoxybenzylmalonate (Ronacare® AP). Corresponding antioxidants, their preparation and use are described in International patent application WO 2006/111233, the disclosure content of which expressly also belongs to the subject-matter of the present application.

The compositions according to the invention may in addition comprise further conventional skin-protecting or skin-care active ingredients. These can in principle be any active ingredients known to the person skilled in the art.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., *Eur. J. Biochem.,* 149 (1985) pages 135-139). Of the pyrimidinecarboxylic acids, particular mention should be made here of ectoin ((S)-1,4,5,6-tetrahydro-2-methyl-4-pyrimidinecarboxylic acid) and hydroxyectoin ((S, S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protection agent in dried yeast and bacteria cells. Pharmaceutical products, such as non-glycosylated, pharmaceutically active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European patent application EP-A-0 671 161 describes, in particular, that ectoin and hydroxyectoin are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula III

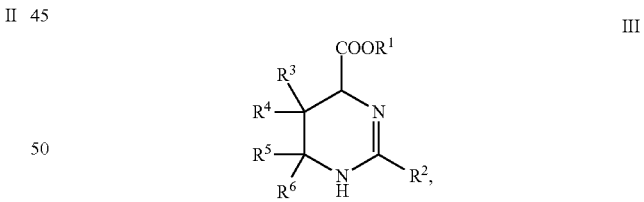

in which $R^1$ is a radical H or C1-8-alkyl, $R^2$ is a radical H or C1-4-alkyl, and $R^3$, $R^4$, $R^5$ and $R^6$ are each, independently of one another, a radical from the group H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S, S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which comprise aryl oximes, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

All compounds or components described here that can be used in the compositions are either known and commercially available or can be synthesised by known processes.

Besides the compounds described here, the compositions according to the invention may also comprise at least one photostabiliser, preferably conforming to the formula IV

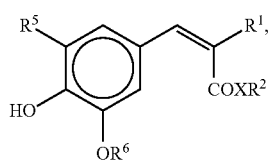

IV where
$R^1$ is selected from —C(O)CH$_3$, —CO$_2$R$^3$, —C(O)NH$_2$ and —C(O)N(R$^4$)$_2$;
X is O or NH;
$R^2$ stands for a linear or branched $C_{1-30}$-alkyl radical;
$R^3$ stands for a linear or branched $C_{1-20}$-alkyl radical;
all $R^4$, independently of one another, stand for H or linear or branched $C_{1-8}$-alkyl radicals;
$R^5$ stands for H, a linear or branched $C_{1-8}$-alkyl radical or a linear or branched —O—$C_{1-8}$-alkyl radical; and
$R^6$ stands for a $C_{1-8}$-alkyl radical;
where the photostabiliser is particularly preferably bis(2-ethylhexyl) 2-(4-hydroxy-3,5-dimethoxybenzylidene)malonate. Corresponding photostabilisers, their preparation and use are described in International patent application WO 03/007906, the disclosure content of which expressly also belongs to the subject-matter of the present application.

The compositions according to the invention can be prepared by processes which are well known to the person skilled in the art, in particular by the processes which serve for the preparation of oil-in-water emulsions or water-in-oil emulsions.

The present invention furthermore relates to a process for the preparation of a composition which is characterised in that at least one particulate UV protection agent is mixed with a cosmetically or dermatologically suitable vehicle, and to the use of particulate UV protection agents for the preparation of a composition having light-protection properties.

These compositions can be, in particular, in the form of simple or complex emulsions (O/W, W/O, O/W/O or W/O/W), such as creams, milks, gels or gel creams, powders and solid sticks, and they may, if desired, be formulated as aerosols and be in the form of foams or sprays. These compositions are preferably in the form of an O/W emulsion.

The cosmetic compositions according to the invention can be used as compositions for protection of the human epidermis and/or of the hair against UV radiation, as sunscreens, in day care or as make-up products.

It should be pointed out that in the sun protection formulations according to the invention which comprise a vehicle of the oil-in-water emulsion type, the aqueous phase (which comprises, in particular, the hydrophilic filters) generally makes up 50 to 95% by weight and preferably 70 to 90% by weight, based on the formulation as a whole, the oil phase (which comprises, in particular, the lipophilic filters) makes up 5 to 50% by weight and preferably 10 to 30% by weight, based on the formulation as a whole, and the (co)emulsifier or (co)emulsifiers make(s) up 0.5 to 20% by weight and preferably 2 to 10% by weight, based on the formulation as a whole.

Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower products. Any desired customary vehicles, assistants and, if desired, further active ingredients may be added to the composition.

Preferred assistants originate from the group of preservatives, antioxidants, stabilisers, solubilisers, vitamins, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerin fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerin, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerin fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:

mineral oils, mineral waxes;

oils, such as triglycerides of capric or caprylic acid, furthermore natural oils, such as, for example, castor oil;

fats, waxes and other natural and synthetic fatty substances, preferably esters of fatty acids with alcohols having a low carbon number, for example with isopropanol, propylene glycol or glycerin, or esters of fatty alcohols with alkanoic acids having a low carbon number or with fatty acids;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acids and saturated and/or unsaturated, branched and/or unbranched alcohols having a chain length of 3 to 30 C atoms. Ester oils of this type can then advantageously be selected from the group of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of branched and unbranched hydrocarbons and hydrocarbon waxes, silicone oils, dialkyl ethers, or the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may advantageously be selected, for example, from the group of synthetic, semi-synthetic and natural oils, for example olive oil, sunflower oil, soya oil, peanut oil, rape-seed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

Cosmetic formulations, which are also part of this invention, may very generally comprise common cosmetic ingredients and additives, particularly the following substances or classes of substance:

Fat-containing substances, cosmetic oils (synthetic and/or natural), organic solvents, both nonionic and ionic (inter alia so-called ionic liquids), hydrophilic, lipophilic or amphiphilic thickeners, softeners, humectants, opacifiers, stabilisers, silicone oils and silicone oil derivatives, antifoam agents, perfume, preservatives, anionic, cationic, nonionic, zwitterionic surfactants, cosmetic active ingredients, fillers, polymers, propellant gases, acids and/or lyes, and any desired substance which is generally used in cosmetics.

Fat-containing substances can be oils or waxes or mixtures thereof. The term oil means substances and compounds which are liquid at room temperature. The term waxes means substances and compounds which have a solid or semisolid consistency and whose melting point is >35° C.

The term oils includes mineral oils (paraffin oils), vegetable oils (such as, for example, jojoba oil), synthetic oils, such as, for example, perhydrosqualenes, fatty alcohols, fatty acids or fatty acid esters, such as, for example, the C12-C15 alkyl benzoate commercially available under the trade name "Witconol TN" from Witco, octyl palmitate, isopropyl lanolate and triglycerides, including capric/caprylic acid triglycerides, silicone oils (cyclomethicone and polydimethylsiloxanes, or PDMS) or fluorinated oils, and polyalkylenes.

Wax constituents of a cosmetic formulation can be, for example, paraffin wax, carnauba wax, beeswax, or hydrogenated castor oil.

The possible organic solvents include, inter alia, lower alcohols and polyols. Polyols can be selected, for example, from the following substances/classes of substance: glycerin, glycol ethers, ethylene glycol, propylene glycol, butylene glycol, dipropylene glycol, diethylene glycol.

Hydrophilic thickeners which can be combined with the UV protection agent according to the invention are selected, for example, from the following group: carboxyvinyl polymers, such as, for example, Carbopols (carbomers) from Noveon and Pemulen products (acrylate/C10-C30-alkyl acrylate copolymer); polyacrylamides, such as, for example, the crosslinked copolymer with the trade name Sepigel 305 (CTFA name: polyacrylamide/C13-14 isoparaffin/Laureth 7) or Simulgel 600 (CTFA name: acryl-amide/sodium acryloyldimethyltaurate copolymer/isohexadecane/polysorbate 80) from SEPPIC; 2-acrylamido-2-methylpropanesulfonic acid polymer and copolymer, which may optionally be crosslinked or neutralised, such as, for example, poly(2-acrylamido-2-methylpropanesulfonic acid), marketed under the trade name "Hostacerin AMPS" (CTFA name: ammonium polyacryldimethyltauramide); cellulose-based derivatives, such as, for example, hydroxyethylcellulose; polysaccharides and in particular xanthan gum; and mixtures thereof.

The lipophilic thickeners mentioned below can also be employed in combination with the substance according to the invention, for example modified alumina, such as, for example, hectorite, and derivatives thereof.

The following cosmetic active ingredients can be employed alone or in combination:
toxin repellents and/or free-radical scavengers;
skin-lightening and/or skin-tanning agents;
antiglycation active ingredients;
NO synthesis inhibitors;

active ingredients for stimulation of the synthesis of dermal and epidermal macromolecules and/or for protection against degradation of these compounds;
active ingredients for stimulation of fibroblast proliferation;
active ingredients for stimulation of keratinocyte proliferation;
muscle-relaxing active ingredients;
tension-increasing and -reducing active ingredients;
skin flake-removing active ingredients;
humectants;
antiinflammatory active ingredients;
active ingredients which have a positive effect on the energy metabolism of the cell;
insect repellents;
substance P or CGRP antagonists.

Emulsifiers which are particularly preferably used for the preparation of W/O emulsions and creams are, inter alia, the following:
Sorbitan glycerol and/or sugar alkyl esters or ethers; silicone surfactants, such as, for example, a mixture of dimethicone copolyol, marketed under the trade name "DC 5225 C" by Dow Corning, and alkyldimethicone copolyols, such as, for example, the laurylmethicone copolyol marketed under the trade name "Dow Corning 5200 Formulation Aid" by Dow Corning; cetyldimethicone copolyol, such as, for example, the commercial product Abil EM 90R from Goldschmidt, a mixture of cetyldimethicone copolyol, consisting of polyglyceryl isostearate (4 mol) and hexyl laurate, marketed under the trade name Abil WE 09 by Goldschmidt.

One or more coemulsifiers may additionally be used in combination with polyol alkyl esters, for example glycerol and/or sorbitan esters, for example polyglyceryl isostearate, which is commercially available under the name Isolan GI 34 from Goldschmidt; sorbitan isostearate, as marketed, for example, under the name Arlacel 987 by Uniqema (Croda); sorbitan glyceryl isostearate, marketed under the trade name Arlacel 986 by Uniqema (Croda), and mixtures thereof.

Examples of suitable emulsifiers for O/W emulsions are nonionic emulsifiers, such as, for example, ethoxylated (especially polyethoxylated) fatty acid esters of glycerin, ethoxylated sorbitan fatty acid esters; ethylenoxylated and/or propylenoxylated fatty acid esters of sugars, such as, for example, sucrose stearate; fatty alcohol ethers of sugar, such as, for example, polyalkylglucosides (APG), such as, for example, decylglucoside and laurylglucoside, as available, for example, under the trade name Plantaren from Cognis. Cetostearyl glucoside pure or as a mixture, such as, for example, in the commercial product Montanov 68 from Seppic; TegoCare CG 90 (Goldschmidt); Emulgade KE3302 (Cognis/Henkel), may also be present. Possible O/W emulsifiers are also formed by compounds of arachidyl glucoside, such as, for example, as a mixture with arachidyl alcohol, behenyl alcohol and arachidyl glucoside, marketed under the trade name Montanov 202 by SEPPIC.

Compositions comprising the UV protection agent according to the invention have a broad range of applications, especially in care and decorative cosmetics. These are suitable for protection of the skin, lips, hair, scalp, hands, nails, eyebrows, eyelids, especially for protection of the areas described against photo- and/or oxidatively induced stress.

The oil phase is advantageously selected from the group of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride, dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane, poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerin, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerin, and, in particular, one or more thickeners, which may advantageously be selected from the group consisting of silicon dioxide, aluminium silicates, polysaccharides and derivatives thereof, for example hyaluronic acid, xanthan gum, hydroxypropyl-methylcellulose, particularly advantageously from the group consisting of the polyacrylates, preferably a polyacrylate from the group consisting of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group consisting of the alkylglucosides, acyl lactylates, betaines and coconut amphoacetates.

The alkylglucosides are themselves advantageously selected from the group consisting of the alkylglucosides which are distinguished by the structural formula

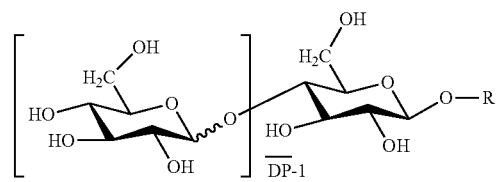

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{10} \cdot 3 + \ldots = \sum \frac{p_i}{100} \cdot i$$

in which $p_1, p_2, p_3 \ldots p_i$ represent the proportion of mono-, di-, tri- . . . i-fold glucosylated products in percent by weight. Products having degrees of glucosylation of 1-2, particularly advantageously of 1.1 to 1.5, very particularly advantageously of 1.2-1.4, in particular of 1.3, are advantageously selected in accordance with the invention.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglucosides which are particularly advantageously used in accordance with the invention are selected from the group of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group of the substances which are distinguished by the structural formula

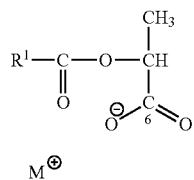

where $R^1$ denotes a branched or unbranched alkyl radical having 1 to 30 carbon atoms, and $M^+$ is selected from the group consisting of the alkali metal ions and the group consisting of ammonium ions which are substituted by one or more alkyl and/or by one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formula

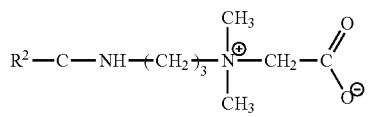

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageously selected in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

An emulsifier that has proven to be particularly preferred in accordance with the invention for O/W emulsions is the commercial product Ceralution C (gemini surfactant) from Sasol.

Co-emulsifiers which are advantageously selected in accordance with the invention are, for example, O/W emulsifiers, principally from the group consisting of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or if isoalkyl derivatives are present, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Compositions which are preferred in accordance with the invention are particularly suitable for protecting human skin against UV-induced ageing processes and against oxidative stress, i.e. against damage caused by free radicals, as are generated, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants that are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerin and sorbitol.

A preferred embodiment of the invention is an emulsion in the form of a protective cream or milk which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Individual emulsifiers may also be mentioned below by way of example of the chemical classes of substance described, which can be employed in combination with the product according to the invention for the preparation of compositions for protection of the skin and hair.

The following products are trademarks of Degussa Goldschmidt:

| | |
|---|---|
| Abil Care 85 | Dimethicone Copolyol (and) Caprylic/Capric Triglycerides |
| Abil EM 90 | Cetyl PEG/PPG-10/1 Dimethicone |
| Abil EM 97 | Bis-PEG/PPG-14/14 Dimethicone (and) Cyclopentasiloxane |
| Abil WE 09 | Polyglyceryl-4 Isostearate (and) Cetyl Dimethicone Copolyol (and) Hexyl Laurate |
| Tego Care 150 | Glyceryl Stearate (and) Steareth-25 (and) Ceteth-20 (and) Stearyl Alcohol |
| Tego Care 215 | Ceteareth-15 (and) Glyceryl Stearate |
| Tego Care 450 | Polyglyceryl-3 Methylglucose Distearate |
| Tego Care CG 90 | Cetearyl Glucoside |
| Tego Care PS | Methyl Glucose Sesquistearate |
| TEGO Care 165 | Glyceryl Stearate (and) PEG-100 Stearate |
| ISOLAN GPS | Polyglyceryl-4 Diisostearate and Polyhydroxystearate Sebacate |
| TEGO Care CE 40 | Cetearyl Alcohol; Palmitamidopropyltrimonium Chloride |
| TEGO SIS 40 | PEG-40 Sorbitan Perisostearate |

The following products are trademarks of Cognis Deutschland:

| | |
|---|---|
| Emulgade F | Cetearyl Alcohol (and) PEG-40 Castor Oil (and) Sodium Sulfate |
| Emulgade 1000Ni | Cetearyl Alcohol (and) Ceteareth-20 |
| Emulgade CM | Cetearyl Isononanoate (and) Ceteareth-20 (and) Cetearyl Alcohol (and) Glyceryl Stearate (and) Glycerin (and) Ceteareth-12 (and) Cetyl Palmitate |
| Eumulgin VL 75 | Lauryl Glucoside (and) Polyglyceryl-2 Dipolyhydroxystearate (and) Glycerin |
| Emulgade sucro | Sucrose Polystearate (and) Hydrogenated Polyisobutene |
| Eumulgin SG | Sodium Stearoyl Glutamate |
| Dehymuls HRE-7 | PEG-7 Hydrogenated Castor Oil |
| Dehymuls LE | PEG-30 Dipolyhydroxystearate |
| Dehymuls PGPH | Polyglyceryl-2 Dipolyhydroxystearate |

The following products are trademarks of Uniqema, Belgium

| | |
|---|---|
| ARLATONE 2121 | Sorbitan Stearate (and) Sucrose Cocoate |
| ARLATONE LC | Sorbitan Stearate (and) Sorbityl Laurate ARLATONE V-100 Steareth-100 (and) Steareth-2 (and) Glyceryl Stearate Citrate (and) Sucrose (and) Mannan (and) Xanthan Gum |
| ARLATONE V-175 | Sucrose Palmitate (and) Glyceryl Stearate (and) Glyceryl Stearate Citrate (and) Sucrose (and) Mannan (and) Xanthan Gum |
| ARLACEL 1689V | Sorbitan Oleate (and) Polyglyceryl-3 Polyricinoleate |
| ARLACEL 1690 | Sorbitan Isostearate (and) Polyglyceryl-3 Polyricinoleate |
| ARLACEL 186 | Glyceryl Oleate (and) Propylene Glycol |
| ARLACEL 481V | Sorbitan Oleate (and) Hydrogenated Castor Oil (and) Beeswax (and) Stearic Acid |
| ARLACEL 582 | Sorbitan Isostearate (and) PEG-2 Hydrogenated Castor Oil (and) Ozokerite (and) Hydrogenated Castor Oil Solid |
| ARLACEL 83V | Sorbitan Sesquioleate |
| ARLACEL 986 | Sorbitan Isostearate (and) Hydrogenated Castor Oil (and) Beeswax (and) Stearic Acid |
| ARLACEL 987 | Sorbitan Isostearate |
| ARLACEL 989 | PEG-7 Hydrogenated Castor Oil |
| ARLACEL P135 | PEG-30 Dipolyhydroxystearate |
| PRISORINE 3700 | Polyglyceryl-3 Diisostearate |
| PRISORINE 3791 | Polyglyceryl-2 Isostearate |
| SPAN 20 | Sorbitan Laurate |
| SPAN 80V | Sorbitan Oleate |
| SPAN 85V | Pharma Sorbitan Trioleate Liquid |

The following products are trademarks of Tri-K Ind.:

| | |
|---|---|
| Biobase EP | Glyceryl Stearate, Cetearyl Alcohol, Sodium Stearoyl Lactylate, Lecithin |
| Biobase RS | Glyceryl Stearate, Cetearyl Alcohol, Sodium Stearoyl Lactylate, Tocopherol |

The following products are trademarks of Vama Farma-Cosmetica Srl

| | |
|---|---|
| Emulvama AGC | Glyceryl Stearate, Cetearyl Alcohol, Stearic Acid, Sodium Cocoyl Glutamate |
| Emulvama AGC | Glyceryl Stearate, Cetearyl Alcohol, Stearic Acid, Sodium Cocoyl Glutamate |
| Emulvama AGW | Sodium Cocoyl Glutamate, Sodium Cocoyl Hydrolyzed Wheat Protein, Disodium Capryloyl Glutamate, Potassium Cocoyl PCA |

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerin, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerin, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or setting a water wave, in the form of a hair lacquer, permanent-waving composition, colorant or bleach for the hair. The composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The following examples explain the present invention in greater detail without restricting the scope of protection. In particular, the features, properties and advantages described in the examples of the compounds on which the relevant examples are based can also be applied to other substances and compounds which are not mentioned in detail, but fall within the scope of protection, unless stated otherwise elsewhere. In addition, the invention can be carried out throughout the range claimed and is not restricted to the examples mentioned here.

The invention is explained in greater detail below with reference to examples.

EXAMPLES

Example 1a

Preparation of Nano-$TiO_2$ 710 ml of sodium titanate (content 100 g of $TiO_2$/l), obtained by reaction of metatitanic acid with sodium hydroxide solution, are diluted with 100 ml of water and decomposed at pH 2.5 by addition of hydrochloric acid with formation of titanium dioxide (rutile). This particulate titanium dioxide obtained by the decomposition is peptised with addition of 115 ml of 30% hydrochloric acid and made up to a total volume of 1000 ml by further addition of water. The peptisation is carried out in a sealed glass flask at 105° C. over a period of 2 h. The product exhibits needle-shaped crystallites.

Example 1b

Preparation of Nano-$TiO_2$

The experimental product from Example 1a is washed to a filtrate conductivity of less than 100 μS/cm and dried.

Example 2a

Coating of Nano-$TiO_2$ with $Al_2O_3$

After completion of the peptisation, 1 l of the experimental product from Example 1a is adjusted to pH=7 using sodium hydroxide solution and heated to 80° C. 40 ml of sodium aluminate solution (content corresponds to 300 g of $Al_2O_3$/l) are subsequently added at constant pH (pH=7; regulation through addition of $H_2SO_4$). When the addition is complete, the mixture is stirred for 2 hours at 80° C. and pH=7.

Example 2b

Coating of Nano-$TiO_2$ with $Al_2O_3$

The experimental product from Example 2a is washed to a filtrate conductivity of less than 100 μS/cm and dried.

Example 3a

Coating of Nano-$TiO_2$ with $Al_2O_3$ and Subsequently $MnO_2$ 1 l of the experimental product from Example 2a is heated to 80° C. 100 ml of an $MnSO_4$ solution (2 g of Mn/l) are subsequently added at constant pH (pH=7; regulation through addition of NaOH). The suspension is stirred for a further 30 min. The product is subsequently washed to a filtrate conductivity of less than 100 μS/cm and dried.

Example 3b

Coating of Nano-$TiO_2$ with $MnO_2$ and Subsequently $Al_2O_3$

After completion of the peptisation, 1 l of the experimental product from Example 1a is heated to 80° C. 100 ml of an $MnSO_4$ solution (2 g of Mn/l) are subsequently added. After a stirring time of 30 min, the suspension is adjusted to pH=7 using sodium hydroxide solution. 40 ml of sodium aluminate solution (corresponding to 300 g of $Al_2O_3$/l) are subsequently added at constant pH (pH=7; regulation through addition of $H_2SO_4$). When the addition is complete, the mixture is stirred for 2 hours at 80° C. and pH=7. The product is subsequently washed to a filtrate conductivity of less than 100 μS/cm and dried.

Example 3c

Coating of Nano-$TiO_2$ with an $Al_2O_3$ and $MnO_2$ Mixture 1 l of the experimental product from Example 1a is heated to 80° C. and neutralised to pH=7 using sodium hydroxide solution. 40 ml of sodium aluminate solution (corresponding to 300 g of $Al_2O_3$/l) and 100 ml of an $MnSO_4$ solution (2 g of Mn/l) are subsequently added simultaneously at constant pH (pH=7; regulation through addition of $H_2SO_4$). When the addition is complete, the mixture is stirred for 2 hours at 80° C. and pH=7. The product is subsequently washed to a filtrate conductivity of less than 100 μS/cm and dried.

Example 3d

Coating of Nano-$TiO_2$ with $Al_2O_3$ and Subsequently Manganese Phosphate 1 l of the experimental product from Example 2a is heated to 80° C. 100 ml of an $MnSO_4$ solution (2 g of Mn/l) and 100 ml of an $Na_3PO_4$ solution (4 g of $Na_3PO_4$/l) are subsequently added simultaneously at constant pH (pH=7; regulation through addition of NaOH/$H_2SO_4$). The suspension is stirred for a further 30 min. The product is subsequently washed to a filtrate conductivity of less than 100 μS/cm and dried.

Example 4a

Coating of Nano-$TiO_2$ with $Al_2O_3$ and Subsequently MnO 1 l of the experimental product from Example 2a is heated to 80° C. 100 ml of an $MnSO_4$ solution (5 g of Mn/l) are subsequently added at constant pH (pH=7; regulation through addition of NaOH). The suspension is stirred for a further 30 min. The product is subsequently washed to a filtrate conductivity of less than 100 μS/cm and dried.

Example 4b

Coating of Nano-$TiO_2$ with $MnO_2$ and Subsequently $Al_2O_3$

After completion of the peptisation, 1 l of the experimental product from Example 1a is heated to 80° C. 100 ml of an MnSO$_4$ solution (5 g of Mn/l) are subsequently added. After a stirring time of 30 min, the suspension is adjusted to pH=7 using sodium hydroxide solution. 40 ml of sodium aluminate solution (corresponding to 300 g of Al$_2$O$_3$/l) are subsequently added at constant pH (pH=7; regulation through addition of H$_2$SO$_4$). When the addition is complete, the mixture is stirred for 2 hours at 80° C. and pH=7. The product is subsequently washed to a filtrate conductivity of less than 100 µS/cm and dried.

Example 4c

Coating of Nano-TiO$_2$ with an Al$_2$O$_3$ and MnO$_2$ Mixture 1 l of the experimental product from Example 1a is heated to 80° C. and neutralised to pH=7 using sodium hydroxide solution. 40 ml of sodium aluminate solution (corresponding to 300 g of Al$_2$O$_3$/l) and 100 ml of an MnSO$_4$ solution (5 g of Mn/l) are subsequently added simultaneously at constant pH (pH=7; regulation through addition of H$_2$SO$_4$). When the addition is complete, the mixture is stirred for 2 hours at 80° C. and pH=7. The product is subsequently washed to a filtrate conductivity of less than 100 µS/cm and dried.

Example 5a

Heat Treatment 100 g of the experimental product from Example 2b are heat-treated at 400° C. for 2 h.

Example 5b

Heat Treatment 100 g of the experimental product from Example 3a are heat-treated at 400° C. for 2 h.

Example 5c

Heat Treatment 100 g of the experimental product from Example 4a are heat-treated at 400° C. for 2 h.

Example 5d

Heat Treatment 100 g of the experimental product from Example 3d are heat-treated at 400° C. for 2 h.

Example 6a

Coating of Nano-TiO$_2$ with SiO$_2$ Followed by MnO$_2$ 1 l of the aqueous, hydrochloric acid suspension of TiO$_2$ from Example 1b is adjusted to a pH of 6.5 using NaOH and heated to 80° C. 52 ml of water-glass solution (corresponding to 384 g of SiO$_2$/l) are subsequently added to the suspension at constant pH (pH=6.5±0.5; regulation through addition of H$_2$SO$_4$). When the addition is complete, the mixture is stirred for 2 hours at 80° C. and pH=6.8. 100 ml of an MnSO$_4$ solution (5 g of Mn/l) are subsequently added at 80° C. and constant pH (pH=7; regulation through addition of NaOH). The suspension is stirred for a further 30 min. The product is subsequently washed to a conductivity of less than 100 µS/cm and dried.

Example 6b

Coating of Nano-TiO$_2$ with SiO$_2$ Followed by MnO$_2$ 1 l of the aqueous, hydrochloric acid suspension of TiO$_2$ from Example 1b is adjusted to a pH of 9.0 using NaOH and heated to 80° C. 52 ml of water-glass solution (corresponding to 384 g of SiO$_2$/l) are subsequently added to the suspension at constant pH (pH=9.0±0.5; regulation through addition of H$_2$SO$_4$). When the addition is complete, the mixture is stirred for 2 hours at 80° C. and pH=6.8. 100 ml of an MnSO$_4$ solution (5 g of Mn/l) are subsequently added at 80° C. and constant pH (pH=7; regulation through addition of NaOH). The suspension is stirred for a further 30 min. The product is subsequently washed to a conductivity of less than 100 µS/cm and dried.

Example 6c

Coating of Nano-TiO$_2$ with SiO$_2$ Followed by MnO$_2$ 1 l of the aqueous, hydrochloric acid suspension of TiO$_2$ from Example 1b is adjusted to a pH of 2.0 using NaOH and heated to 80° C. 52 ml of water-glass solution (corresponding to 384 g of SiO$_2$/l) are subsequently added to the suspension at constant pH (pH=2.0±0.5; regulation through addition of H$_2$SO$_4$). When the addition is complete, the mixture is stirred for 2 hours at 80° C. and pH=6.8. 100 ml of an MnSO$_4$ solution (5 g of Mn/l) are subsequently added at 80° C. and constant pH (pH=7; regulation through addition of NaOH). The suspension is stirred for a further 30 min. The product is subsequently washed to a conductivity of less than 100 µS/cm and dried.

Example 6d

Coating of Nano-TiO$_2$ with SiO$_2$ Followed by MnO$_2$ 1 l of the aqueous, hydrochloric acid suspension of TiO$_2$ from Example 1b is adjusted to a pH of 9.0 using NaOH and heated to 80° C. 52 ml of water-glass solution (corresponding to 384 g of SiO$_2$/l) are subsequently added to the suspension. During this addition, the pH rises to about 10.6. When the addition is complete, the pH is lowered to 6.5 by addition of sulfuric acid, and the mixture is then stirred for 2 hours at 80° C. and pH=6.8. 100 ml of an MnSO$_4$ solution (5 g of Mn/l) are subsequently added at 80° C. and constant pH (pH=7; regulation through addition of NaOH). The suspension is stirred for a further 30 min. The product is subsequently washed to a conductivity of less than 100 µS/cm and dried.

Example 6e

Coating of Nano-TiO$_2$ with SiO$_2$ (Comparison to 6a)

1 l of the aqueous, hydrochloric acid suspension of TiO$_2$ from Example 1b is adjusted to a pH of 6.5 using NaOH and heated to 80° C. 52 ml of water-glass solution (corresponding to 384 g of SiO$_2$/l) are subsequently added to the suspension at constant pH (pH=6.5±0.5; regulation through addition of H$_2$SO$_4$). When the addition is complete, the mixture is stirred for 2 hours at 80° C. and pH=6.8. The product is subsequently washed to a conductivity of less than 100 μS/cm and dried.

Comparative Example 7

The Mn-doped titanium dioxide grade Oxonica Optisol™ (current market product from Oxonica on the date of filing).

Comparative Example 8

Rutile $TiO_2$ having a BET of 100 m²/g prepared as described in WO 99/60994, Example 3.

Comparative Example 9

Degussa P25 (rutile/anatase) having a BET of 50 m²/g.

Example 10

Characterisation of the Products According to the Invention

The advantageous properties of the products according to the invention can be demonstrated, in particular, using the following methods:
Method 10a: Spin Concentration of DPPH- or TPA-Containing Samples by Means of Continuous Wave EPR Measurement The free-radical-reducing action of the products according to the invention can be demonstrated, for example, on the 2,2-diphenyl-1-picrylhydrazyl (DPPH) free radical or on the 2,2,5,5-tetramethylpyrrolin-1-yloxyl-3-acetylene (TPA) free radical.
Nomenclature:
The samples have the following assignments

| Sample No. | Sample description |
| --- | --- |
| 1 | $TiO_2$ rutile parent substance without coating |
| 2 | Microrutile without Fe doping and without $Al_2O_3$ aftertreatment with 1% Mn doping, heat-treated at 700° C. |
| 3 | Microrutile with 0.1% Fe doping and 12% $Al_2O_3$ aftertreatment |
| 4 | Microrutile with 0.1% Fe doping and 12% $Al_2O_3$ aftertreatment |
| 5 | Microrutile without Fe doping and without $Al_2O_3$ aftertreatment |
| 6 | Microrutile with 0.1% Fe doping and 12% $Al_2O_3$ aftertreatment with 0.2% Mn precipitation |
| 8 | Microrutile with 0.1% Fe doping and 12% $Al_2O_3$ aftertreatment with 0.5% Mn precipitation, heat-treated at 400° C. for 2 h |
| 9 | Microrutile with 0.1% Fe doping and 12% $Al_2O_3$ aftertreatment with 0.5% Mn precipitation, heat-treated at 800° C. for 2 h |
| 10 | Optisol ® from Oxonika; Batch 210 |
| 11 | Eusolex ® T-2000 standard product Batch K92002673; Merck |

Measurement Series:
  Series 0: pure pigment samples
  Series 1: DPPH+ pigment sample after a reaction time of three minutes
  Series 2: TPA+ pigment sample after a reaction time of three minutes
  Series 3: DPPH+ pigment sample after a reaction time of 96 hours Sample Preparation:
The samples are suspended in perdeuterated toluene so that the concentration is about 100 μM. The DPPH and TPA solutions are likewise prepared in a concentration of 100 μM in perdeuterated toluene. For the DPPH measurement series, in each case 60 μl of the samples are combined with 60 μl of DPPH solution in an Eppendorf cup, and 100 μl are transferred into an EPR sample tube. The resultant EPR sample is saturated with argon for 3 minutes. The DPPH reference sample is prepared analogously with 60 μl of perdeuterated toluene. The same procedure is followed for the TPA measurement series. The EPR measurements on DPPH-containing samples are repeated after a reaction time of 96 hours.
Method:
Under identical measurement parameters, the intensity of the resultant continuous wave EPR absorption signal is dependent on the spin concentration of the sample. The integral of the absorption signal is thus a measure of the spin concentration of the sample. However, the first derivative of the absorption spectrum is measured on the basis of a technical amplification method. Information on the spin concentration is then possible by means of double integration. Comparative measurements on a reference sample which comprises only DPPH or TPA against samples which comprise both DPPH or TPA and also the test substances are measured. The resultant double integrals are compared to one another. In each measurement series, the DPPH or TPA reference sample is measured three times and the arithmetic mean of double integrals is used.
Measurement Parameters:
The spectra are recorded on a standard Bruker E500 X-Band cw spectrometer at room temperature under the following parameters:
Pure Pigment Samples: (Series 0)

| T: | RT | freq.: | 9.4283 GHz |
| --- | --- | --- | --- |
| field: | 480 G-6500 G | delay: | 8 s |
| points: | 4096 | scan: | 1 |
| microwave: | 23 dB | receiver gain: | 60 dB |
| mod. freq.: | 100 kHz | mod. amp.: | 1 G |
| time const.: | 81.92 ms | conv. time: | 81.92 ms |
| sweep time: | 335.54 s | Q: | ~2500-2700 |

DPPH+Pigment After Reaction for 3 min: (Series 1)

| T: | RT | freq.: | 9.4283 GHz |
| --- | --- | --- | --- |
| field: | 480 G-6500 G | delay: | 8 s |
| points: | 4096 | scan: | 1 |
| microwave: | 23 dB | receiver gain: | 60 dB |
| mod. freq.: | 100 kHz | mod. amp.: | 1 G |
| time const.: | 81.92 ms | conv. time: | 81.92 ms |
| sweep time: | 335.54 s | Q: | ~2500-2700 |

TPA+Pigment After Reaction for 3 min: (Series 2)

| T: | RT | freq.: | 9.4270 GHz |
| --- | --- | --- | --- |
| field: | 3320 G-3390 G | delay: | 3 s |
| points: | 1024 | scan: | 10 |
| microwave: | 23 dB | receiver gain: | 55 dB |
| mod. freq.: | 100 kHz | mod. amp.: | 1 G |
| time const.: | 40.96 ms | conv. time: | 40.96 ms |
| sweep time: | 41.94 s | Q: | ~2500-2700 |

DPPH+Pigment After Reaction for 96 h: (Series 3)

| T: | RT | freq.: | 9.4266 GHz |
|---|---|---|---|
| field: | 3325 G-3395 G | delay: | 3 s |
| points: | 1024 | scan: | 5 |
| microwave: | 23 dB | receiver gain: | 55 dB |
| mod. freq.: | 100 kHz | mod. amp.: | 0.5 G |
| time const.: | 81.92 ms | conv. time: | 81.96 ms |
| sweep time: | 83.89 s | Q: | ~2500-2900 |

Results:
The results are summarised in the following table and FIG. 1:

TABLE

Spin concentration of the samples investigated

| Sample | Series 1 [%] | Error [%] | Series 2 [%] | Error [%] | Series 3 [%] | Error [%] |
|---|---|---|---|---|---|---|
| 1 | 79.68 | 20.88 | 85.98 | 22.53 | 71.58 | 18.78 |
| 2 | 53.00 | 13.89 | 103.20 | 27.03 | 110.9 | 29.05 |
| 3 | 36.33 | 9.52 | 89.13 | 23.35 | 73.70 | 19.31 |
| 4 | 62.15 | 16.28 | 93.79 | 24.57 | 97.88 | 25.64 |
| 5 | 50.18 | 13.15 | 87.27 | 22.86 | 99.46 | 26.06 |
| 6 | 25.06 | 6.56 | 91.85 | 24.07 | 67.66 | 17.73 |
| 8 | 39.43 | 10.33 | 99.23 | 26.00 | 44.22 | 11.58 |
| 9 | 37.43 | 9.81 | 93.14 | 24.40 | 96.41 | 25.26 |
| 10 | 53.96 | 14.14 | 96.22 | 25.21 | 107.30 | 28.12 |
| 11 | 52.55 | 13.77 | 88.92 | 23.30 | 116.60 | 30.56 |

Method 10b: Rancimat Test 1.5 g of $TiO_2$ (see table) are stirred for 15 minutes at RT by means of a magnetic stirrer with 10.5 g of unstabilised soya oil (supplier Gustav Hees). In each case 4 g of the resultant suspensions are used for the measurement. (The samples are stored in the cool and dark until commencement of the measurement.)

The respective samples are transferred into a reaction vessel in a Rancimat 679 (Metrohm) with evaluation unit and plotter (reaction temperature 120° C., air throughput 15 scale units). The decomposition of the soya oil occurs earlier or later depending on the addition ($TiO_2$). The determination of these decomposition products compared with pure soya oil is carried out by detection of gases forming, which are expelled in the stream of air and dissolved in water, by means of conductivity measurement.

A relative protection factor compared with pure soya oil can thus be determined.

Relative protection factor of unstabilised soya oil=1

Relative protection factor <1 means substance is pro-oxidative

Relative protection factor >1 means substance is antioxidative

| Sample | Relative stability compared with unstabilised soya oil |
|---|---|
| Example 2b | >2.5 |
| Example 6e | >2.5 |
| Example 7 | 0.35 |

Method 10c: Assessment of the Product Colour

The assessment can be carried out on a powder disc or in a formulation. The assessment is carried out using a colorimeter (for example Macbeth Color Eye 7000 spectrophotometer) with standard illuminant D65/10° with no gloss. The colour separations delta L* are calculated from the remissions in accordance with DIN 6174 as the lightness difference of the sample relative to Example 2b.

| Product colour Powder disc (delta L* in accordance with DIN 6174) Titanium dioxide type | |
|---|---|
| Example 1b | +0.9 |
| Example 2b | 0 (reference) |
| Example 3a | −4.7 |
| Example 3b | −6.1 |
| Example 3c | −5.5 |
| Example 3d | −7.2 |
| Example 4a | −7.8 |
| Example 4b | −9.8 |
| Example 4c | −5.1 |
| Example 5a | −0.3 |
| Example 5b | −6.4 |
| Example 5c | −8.9 |
| Example 5d | −10.4 |
| Example 6a | −3.7 |
| Example 6e | +1.5 |
| Example 7 | −14.7 |
| Example 8 | −29.2 |
| Example 9 | −30.7 |

The assessment of the product colour in formulations is carried out with reference to the following formulation:

| Raw material (INCI) | % by wt. |
|---|---|
| Titanium Dioxide, per example | 5 |
| PEG-100 Stearate, Glyceryl Stearate | 10 |
| PARAFFINUM LIQUIDUM (MINERAL OIL) | 25 |
| CETYL ALCOHOL | 2 |
| LANOLIN ANHYDROUS | 2 |
| BHT (and) GLYCERYL STEARATE (and) GLYCERYL OLEATE (and) ASCORBYL PALMITATE (and) CITRIC ACID (and) PROPYLENE GLYCOL | 0.05 |
| PROPYLPARABEN | 0.05 |
| SORBITOL | 3 |
| GLYCERIN | 2 |
| DISODIUM EDTA | 0.05 |
| METHYLPARABEN | 0.15 |
| AQUA (WATER) | to 100 |

| Product colour Formulation (delta L* in accordance with DIN 6174) Titanium dioxide type | |
|---|---|
| Example 3a | −5.2 |
| Example 4a | −7.8 |
| Example 7 | −19 |

The product colour of the formulation comprising the products according to the invention is significantly lighter than the comparative formulation comprising the market product from Comparative Example 7. The results are also shown in FIG. 3.

Method 10d: UV Absorption of a Surface Coating
Preparation of the Surface Coating:
Millbase A:

| | |
|---|---|
| Acrylate binder (Macrynal SM 510 n; Cytec Surface Specialities) | 36.30 g |

-continued

| | |
|---|---|
| Xylene/methoxypropyl acetate 2:1 | 43.27 g |
| Product | 42.00 g |

All ingredients are weighed out to an accuracy of 0.05 g into a 300 ml PE wide-necked bottle, and 300 g (±3 g) of glass beads (diameter 2 mm) are added.

After brief shaking by hand (about 10 sec.), the Kautex bottles are clamped into a shaking machine and shaken for 90 min.

Auxiliary Solution B:

| | |
|---|---|
| Dibutyltin(IV) dilaurate (brand DBTL; Cromption Vinyl Additives) (1% in xylene) | 0.94 g |
| Diethylethanolamine | 1.68 g |
| Silicone oil L 050; Wacker Chemie | 4.41 g |
| Solvesso 100; Exxon Mobil Chemical | 24.67 g |
| Xylene | 28.64 g |
| Methoxypropyl acetate | 39.66 g |
| All ingredients are homogenised. | |
| Surface-coating formulation | |
| Acrylate binder (Macrynal SM 510 n; Cytec Surface Specialities) | 39.90 g |
| Millbase A | 2.00 g |
| Isocyanate binder (Desmodur N 75; Bayer) | 17.21 g |
| Auxiliary solution B | 19.74 g |
| Xylene/methoxypropyl acetate 2:1 | 21.15 g |

For production of the test coatings, millbase A is admixed homogeneously with the surface-coating formulation by manual stirring after the other components of the surface-coating formulation have been mixed.

Determination of the UV Absorption (Decadic Absorption Coefficient at 300 nm and 560 nm)

The surface-coating formulation is applied to an acetate film having a thickness of 60 μm using a spiral doctor blade (60 μm). After a drying time of 5 min, the coating is force-dried at 80° C. for about 30 min. The absorbance measurement is carried out on a UV-VIS spectrometer at 300 nm and 560 nm.

The decadic absorption coefficient is calculated as follows:

$c_{sample}$=concentration of the sample investigated from examples in g per l (solid)

$d_{sample}$=dry-layer thickness of the surface coating applied to acetate film in cm $E_{sample}$=absorbance of the surface coating comprising sample from examples $E_{varnish}$=absorbance of the varnish $E_{sample}$=decadic absorption coefficient (L g$^{-1}$ cm$^{-1}$) at the corresponding wavelength $$\varepsilon_{sample} = \frac{(E_{sample} - E_{varnish})}{c_{sample} \times d_{sample}}$$

The value at 300 nm indicates the UV protection performance. The higher the value, the better the UV protection.

The value at 560 nm indicates the transparency of the product. The lower the value, the more transparent the product (a sample having a value of 0.6 is 4× as transparent as a sample having a value of 2.4).

| Sample | Dec. absorption coefficient at 300 nm | Dec. absorption coefficient at 560 nm |
|---|---|---|
| Example 2b | 47 | 0.63 |
| Example 4a | 46 | 0.64 |
| Example 8 | 34 | 2.38 |
| Example 9 | 18 | 4.22 |

Method 10e: Transparency in the Visible Region (at Wavelength 560 nm)

The surface coating comprising millbase A from method 10d is applied to an acetate film having a thickness of 60 μm using a spiral doctor blade (60 μm). After a drying time of 5 min, the coating is force-dried at 80° C. for about 30 min.

The transparency measurement is carried out using a UV-VIS spectrometer at 560 nm. The transparency of the acetate film coated with a varnish (without sample) is set at 100%.

| Sample | Transparency in the visible region (at wavelength 560 nm) |
|---|---|
| Example 2b | 96.3% |
| Example 4a | 96.2% |
| Example 8 | 86.7% |
| Example 9 | 77.6% |

Method 10f: In Vitro SPF Determination Analogously to DIN 67502

Test Formulation

| Raw material (INCI) | % by wt. |
|---|---|
| PEG-100 STEARATE, GLYCERYL STEARATE | 10 |
| PARAFFINUM LIQUIDUM (MINERAL OIL) | 25 |
| CETYL ALCOHOL | 2 |
| LANOLIN ANHYDROUS | 2 |
| BHT (and) GLYCERYL STEARATE (and) GLYCERYL OLEATE (and) ASCORBYL PALMITATE (and) CITRIC ACID (and) PROPYLENE GLYCOL | 0.05 |
| PROPYLPARABEN | 0.05 |
| Titanium dioxides according to examples | 5 |
| SORBITOL | 3 |
| GLYCERIN | 2 |
| DISODIUM EDTA | 0.05 |
| METHYLPARABEN | 0.15 |
| AQUA (WATER) | to 100 |

| Test formulation comprising 5% of sample from | In vitro SPF 0.75 mg/cm$^2$ on PMMA |
|---|---|
| Example 2b | 8 |
| Example 4a | 8 |
| Example 7 | 3.5 |

Method 10g:

The amount of UV-induced free radicals (FR) is determined in a pig skin biopsy. To this end, the skin is marked with a skin free-radical indicator. The FR react with the sample (emulsion comprising TiO$_2$) and oxidise the latter. The residual content of free-radical indicator is determined by means of ESR (electron spin resonance spectroscopy). Only free radicals from the interior of the skin oxidise this free-radical indicator. The RSF quantifies this amount of free radicals and gives an indication of how much longer an individual can remain in the sun for the same free-radical formation (RSF 2=reduction by 50% of free radicals).

Procedure:

The formulation is applied to the epidermal side of a pig skin biopsy (2 mg/cm$^2$) and stored in the dark for 15 minutes. The skin biopsy is then incubated for 5 minutes with the epidermal side up on a filter paper impregnated with a free-radical indicator.

A skin cut-out (diameter 4 mm) is prepared and irradiated with 1.2 MED.

ESR measurement: the reaction of the free-radical indicator with the sample reduces the ESR signal.

Calculation of the RSF:

$$RSF = \frac{N_{free\ radicals} \text{unprotected}}{N_{free\ radicals} \text{protected}}$$

RSF Results (after 1.2 MED UV Irradiation):

| | |
|---|---|
| Placebo O/W formulation without TiO$_2$ | 1 |
| 5% of Example 9 | 2.8 |
| 5% of Example 2a | 4.6 |
| 5% of Example 7 | 4.9 |
| 5% of Example 3a | 6.4 |
| 5% of Example 4a | 7.4 (=84% reduction in free radicals compared with placebo). |

It can be seen from this that Examples 3a/4a according to the invention have a strong free-radical-scavenging potential.

Method 10h:

Efficacy test in vivo against photooxidative stress of the skin, induced by UVA irradiation—the "β-carotene test".

The in-vivo efficacy of the products according to the invention in the test formulation is tested as described in method 10c and g.

The formulation is tested on 10 healthy people, both male and female with an age above 18 years. 2 mg/cm$^2$ of formulation are applied to the inside of the forearm in an area of 35 cm$^2$. After 20 minutes, 80 µl of a β-carotene solution are applied (5 mg/100 ml in n-hexane or a supersaturated and filtered solution in n-hexane), and the UVA irradiation (10 J/cm$^2$) begins 3 minutes later. The change in colour is measured by determining the b* value compared with a test area changed in colour by β-carotene without application of the formulation, as described above. The b* value is measured via a chromameter.

Chromameter Measurement

The colour evaluation was carried out with the aid of the Minolta CR-300 Chromameter. Chromameters are colorimeters which were originally employed in industry in the area of paint manufacture and paint processing. With the aid of these instruments, different colour shades can be represented precisely and numerically [60]. A suitable colour system is the colour standard system [6] developed by the Commission Internationale de l'Eclairage (CIE) in 1976, which, in a similar way to colour processing by the human eye, is based on the three-region method with the primary colours red, green and blue. Each hue can be determined precisely by a vectorial representation in a three-dimensional system with the coordinates L* (lightness), a* (red-green) and b* (yellow-blue).

In addition, the L*a*b* system is the most similar to the visually perceived colour separations. Owing to these basic principles in parallel to the physiological colour processing system, these industrially employed colorimeters can likewise be used in dermatology for assessing skin colour and have also already successfully been used in the past for the measurement of cutaneous colour differences [5], [11], [12], [14], [17], [18], [20], [23], [47].

5. Chan, S. Y., Li Wan Po, A. Quantitative evaluation of drug-induced erythema by using a tristimulus colour analyzer: experimental design and data analysis. Skin. Pharmacol. 6 (1993) 298-312

11. Eckhardt, L., Mayer, J. A., Creech, L., Johnston, M. R., Lui, K. J., Sallis, J. F., Elder, J. P. Assessing children's ultraviolet radiation exposure: the potential usefulness of a colorimeter. Am. J. Public Health 86 (1996) 1802-1804

12. Fluhr, J. W., Pfisterer, S., Gloor, M. Direct comparison of skin physiology in children and adults with bioengineering methods. Pediatr. Dermatol. 17 (2000) 436-439

14. Fullerton, A., Benefeldt, E., Petersen, J. R., Jensen, S. B., Serup, J. The calcipotrion dose-irritation relationship: 48 hour occlusive testing in healthy volunteers using Finn Chambers. Br. J. Dermatol. 138 (1998) 259-265

17. Garigue, J., Marguery, M. C., Malmary, M. F., el Sayed, F., Bazex, J. Measurement of actinic erythema in healthy subjects and in subjects with polymorphous light eruption using a tristimulus colorimeter. Dermatology 190 (1995) 31-34

18. Gassmueller, J., Maas-Irslinger, R., Rippke, F., Tausch, I. Antiinflammatorische Wirksamkeit magistraler Rezepturen mit Glukokortikosteroiden in Eucerinum-Fertiggrundlagen im Vergleich zu Fertigpräparaten im UVB-Erythemtest [Antiinflammatory Efficacy of Magistral Formulations Comprising Glucocorticosteroids in Eucerinum Ready-Prepared Vehicles Compared with Ready-Made Preparations in the UVB Erythema Test]. Zeitschrift für Hautkrankheiten, H+G 6 (1998) 364-370

20. Guarrera, M., Brusati, C., Rebora, A. Topical metronidazole does not abate UVB-induced erythema. Dermatology 203 (2001) 121-123

23. Henry, F., Fumal, I., Pierard, G. E. Postural skin colour changes during the corticosteroid blanching assay. Skin. Pharmacol. Appl. Skin. Physiol. 12 (1999) 199-210

47. Seitz, J. C., Whitmore, C. G. Measurement of erythema and tanning responses in human skin using a tristimulus colorimeter. Dermatologica 177 (1988) 70-75

60. Tronnier, M., Schulz, R., Wolff, H. H. Colorimetrische Erythemmessung nach UVB-Bestrahlung an gesunder Haut in Abhängigkeit von unterschiedlicher Vorbehandlung [Colorimetric Erythema Measurement after UVB Irradiation on Healthy Skin as a Function of Different Pretreatment]. Akt. Dermatol. 18 (1992) 183-186

The results are expressed as the rate of inhibition compared with an untreated area. The colour index in % corresponds directly to the efficacy against free radicals.

$$\text{colour index} = 100 - \left( \frac{sample_{coloured} - sample_{irradiated}}{control_{coloured} - control_{irradiated}} \times 100 \right)$$

Coloured means the colour determined after colouring with beta-carotene. Irradiated means the colour determined after colouring and irradiation.

Results:
  Example 2b—47%
  Example 3a—48%
  Example 4a—61%
  Example 9—17%.

The results are shown graphically in FIG. 2.

The results confirm the excellent photoprotective efficacy of the products according to the invention in vivo.

Formulation Example 1

Sunscreen Soft Cream (O/W)

| Raw material (INCI) | % by wt. |
|---|---|
| A | |
| Product from Example 3a | 3.00 |
| Steareth-10, Steareth-7, Stearyl alcohol | 2.00 |
| Glyceryl stearate, Ceteth-20 | 2.00 |
| Glyceryl stearate | 3.00 |
| Microwax | 1.00 |
| Oleyl oleate | 6.00 |
| Cetearyl octanoate | 14.00 |
| Caprylic/capric triglyceride | 4.00 |
| Propylparaben | 0.05 |
| B | |
| Propylene glycol | 4.00 |
| Allantoin | 0.20 |
| Water | 60.60 |
| Methylparaben | 0.15 |

Preparation:

Heat phase A and phase B to 80° C. Slowly add phase B to phase A with stirring, homogenise and cool with stirring.

Formulation Example 2

Sunscreen Spray Lotion (O/W)

| Raw material (INCI) | % |
|---|---|
| A | |
| Ethylhexyl methoxycinnamate, BHT | 5.00 |
| Product from Example 3b | 4.00 |
| Glyceryl stearate, cetyl alcohol, PEG-75 stearate, ceteth-20, steareth-20 | 3.30 |
| PPG-1-PEG-9 lauryl glycol ether | 0.50 |
| Diisostearoyl trimethylolpropane Siloxy silicate | 1.50 |
| $C_{12-15}$ alkyl benzoate | 3.00 |
| Dioctyl adipate | 4.00 |
| Dimethicone | 2.00 |
| B | |
| Dimethicone copolyol phosphate | 2.50 |
| Butylene glycol | 2.50 |
| Water | 70.50 |
| C | |
| PPG-1 Trideceth-6, polyquaternium-37, propylene glycol dicaprylate/dicaprate | 0.47 |
| D | |
| Propylene glycol, DMMDM hydantoin, methylparaben, propylparaben | 0.73 |

Preparation:

Combine phase A apart from the titanium dioxide and heat to 60° C. Slowly incorporate titanium dioxide into the molten oil phase. Heat phase B to 60° C., then disperse phase C in with stirring. Stir phase A into phase B/C with high input of energy. Cool with stirring, and add phase D at 40° C. Homogenise and cool to 25° C. with stirring.

Formulation Example 3

Sunscreen Soft Cream (O/W)

| Raw material (INCI) | % |
|---|---|
| A | |
| Product from Example 3c | 10.00 |
| Steareth-10, steareth-7, stearyl alcohol | 3.00 |
| Glyceryl stearate, ceteth-20 | 3.00 |
| Glyceryl stearate | 3.00 |
| Microwax | 1.00 |
| Oleyl oleate | 4.00 |
| Cetearyl octanoate | 10.50 |
| Caprylic/capric triglyceride | 4.00 |
| Propylparaben | 0.05 |
| B | |
| Propylene glycol | 4.00 |
| Allantoin | 0.20 |
| Water | 57.10 |
| Methylparaben | 0.15 |

Preparation:

Heat phases A and B to 80° C. Slowly add phase B to phase A with stirring, homogenise and cool with stirring.

Formulation Example 4

Sunscreen Lotion (O/W)

| Raw material (INCI) | % |
|---|---|
| A | |
| Ethylhexyl methoxycinnamate, BHT | 6.00 |
| Butyl methoxydibenzoylmethane | 1.00 |
| Polyglyceryl-3 methylglucose distearate | 4.00 |
| Ethylhexyl stearate | 8.00 |
| Cetearyl isononanoate | 2.00 |
| PVP/eicosene copolymer | 1.00 |
| Tocopheryl acetate | 1.00 |
| B | |
| Xanthan gum | 0.30 |
| Sodium cetearyl sulfate | 1.00 |
| Glycerin | 5.00 |
| Water | 65.70 |
| C | |
| Product from Example 4a | 4.00 |
| D | |
| Phenoxyethanol, butylparaben, ethylparaben, propylparaben, methylparaben | 1.00 |

Preparation:

Heat phase A to 80° C. Pre-swell the Keltrol of phase B in the water, then add the remaining raw materials and heat to 80° C. Add phase A to phase B and homogenise for 2 min. (rod mixer): cool with stirring and add phase C at 35° C.

Homogenise again for 1 min. (rod mixer). Cool to room temperature and stir in phase D.

Formulation Example 5

Sunscreen Lotion (O/W)

| Raw material (INCI) | % |
|---|---|
| A | |
| Product from Example 3d | 5.00 |
| Ethylhexyl methoxycinnamate, BHT | 5.00 |
| Glyceryl stearate, cetyl alcohol, PEG-75 stearate, ceteth-20, stearate-20 | 3.30 |
| PPG-1-PEG-9 lauryl glycol ether | 0.50 |
| Diisostearoyl trimethylolpropane siloxy silicate | 1.50 |
| C12-15 Alkyl benzoate | 3.00 |
| Dioctyl adipate | 4.00 |
| Dimethicone | 2.00 |
| B | |
| Ectoin | 0.10 |
| Allantoin | 0.20 |
| Dimethicone copolyol phosphate | 2.50 |
| Butylene glycol | 2.50 |
| Water | 68.90 |
| C | |
| PPG-1 trideceth-6, polyquaternium-37, propylene glycol dicaprylate/dicaprate | 0.47 |
| D | |
| Propylene glycol, DMMDM hydantoin, ethylparaben | 0.73 |
| Perfume | 0.30 |

Preparation:

Combine phase A apart from the titanium dioxide and heat to 60° C. Slowly incorporate titanium dioxide into the molten oil phase. Heat phase B to 60° C., then disperse phase C in with stirring. Stir phase A into phase B/C with vigorous stirring. Cool with stirring and add phase D at 40° C. Homogenise and cool to 25° C. with stirring.

Formulation Example 6

Sunscreen Lotion (O/W)

| Raw material (INCI) | % |
|---|---|
| A | |
| Product from Example 4a or 4b | 5.00 |
| Butylmethoxydibenzoylmethane | 3.00 |
| Steareth-10, steareth-7, stearyl alcohol | 3.00 |
| Glyceryl stearate, ceteth-20 | 3.00 |
| Glyceryl stearate | 3.00 |
| Microwax | 1.00 |
| Oleyl oleate | 4.43 |
| Cetearyl octanoate | 11.64 |
| Caprylic/capric triglyceride | 4.43 |
| Propylparaben | 0.05 |
| B | |
| Propylene glycol | 4.00 |
| Allantoin | 0.20 |
| Water | 57.10 |
| Methylparaben | 0.15 |

Preparation:

Heat phases A and B to 80° C. Slowly add phase B to phase A with stirring, homogenise and cool with stirring.

Formulation Example 7

Sunscreen Lotion (O/W) SPF 10 (Sun Protection Factor, Colipa Method with 10 Test Subjects)

| | |
|---|---|
| A | |
| Steareth-10, steareth-7, stearyl alcohol | 3.00 |
| Glyceryl stearate, ceteth-20 | 3.00 |
| Cetearyl octanoate | 15.50 |
| Glyceryl stearate | 3.00 |
| Oleyl oleate | 7.00 |
| Microwax | 1.00 |
| Caprylic/capric triglyceride | 6.00 |
| Propylparaben | 0.05 |
| B | |
| 33% aqueous dispersion of the product from Example 5a | 16.70 |
| Propylene glycol | 4.00 |
| Allantoin | 0.20 |
| Water | 40.40 |
| Methylparaben | 0.15 |

Preparation:

Heat phase A to 75° C. and phase B to 80° C. Slowly stir phase B into phase A. Homogenise and cool with stirring.

Formulation Example 8

Sunscreen spray lotion (O/W)

| | |
|---|---|
| A | |
| Product from Example 5d | 5.00 |
| Ethylhexyl methoxycinnamate, BHT | 7.50 |
| Benzophenone-3 | 2.50 |
| PEG-100 stearate, glyceryl stearate | 2.80 |
| PPG-1-PEG-9 lauryl glycol ether | 0.40 |
| Dicapryl ether | 4.50 |
| Steareth-10 | 0.50 |
| Stearyl alcohol | 0.60 |
| Dimethicone | 2.00 |
| B | |
| Dimethicone copolyol phosphate | 2.50 |
| Chitosan glycolate | 2.00 |
| Glycerin | 2.50 |
| Water | 66.10 |
| C | |
| PPG-1 trideceth-6, polyquaternium-37, propylene glycol dicaprylate/dicaprate | 0.40 |
| D | |
| Propylene glycol, DMMDM hydantoin, methylparaben, propylparaben | 0.70 |

Preparation:

Combine phase A apart from the titanium dioxide and heat to 60° C. Slowly incorporate titanium dioxide into the molten oil phase. Heat phase B-1 to 60° C., then disperse phase B-2 in with stirring. Stir phase A into phase B with high input of energy. Cool with stirring, and add phase C at 40° C. Homogenise and cool to 25° C. with stirring.

Formulation Example 9

Sunscreen Cream, High SPF, Water-Resistant (O/W)

| Raw material (INCI) | % |
|---|---|
| A | |
| Water | 38.30 |
| Glycerin | 3.00 |
| Pentylene glycol | 3.00 |
| PVP/hexadodecene copolymer | 1.00 |
| Sodium cetearyl sulfate | 1.00 |
| Xanthan gum | 0.20 |
| B | |
| Glyceryl stearate, cetearyl alcohol, sodium stearoyl lactylate, tocopherol | 5.00 |
| Tri-C12-13 alkyl citrate | 3.50 |
| Isopropylphthalimide, butylphthalide | 5.00 |
| Caprylic/capric triglyceride | 2.50 |
| C12-15 alkyl benzoate | 2.00 |
| Cyclomethicone | 0.80 |
| Tocopheryl acetate | 1.00 |
| Butylmethoxydibenzoylmethane | 1.00 |
| Benzophenone-3 | 2.00 |
| Product from Example 4c | 4.00 |
| C | |
| Water, ethylhexyl methoxycinnamate, silica, PVP, chlorophenesin, BHT (Eusolex UV Pearl OMC) | 20.00 |
| D | |
| Carbomer | 0.15 |
| Water | 4.85 |
| E | |
| Sodium hydroxide | 0.90 |
| F | |
| Phenoxyethanol, butylparaben, ethylparaben, propylparaben, methylparaben | 0.50 |
| Perfume | 0.30 |

Preparation:

Heat phases A and B to 80° C. separately from one another. Homogenise phase B using the Turrax until the pigment is well wetted. Add phase B to phase A and homogenise for 2 min. Cool to 35° C., add phase C and homogenise for 30 sec. Add phase D and homogenise for 30 sec. Stir in phase E and neutralise using phase F and homogenise until satisfactory pigment distribution has been achieved (microscopic check!). Cool to room temperature, deaerate and stir in phase G.

Formulation Example 10

Sun Protection Lotion (PEG-Free) In Vitro SPF 12±2

| Raw material (INCI) | % |
|---|---|
| A | |
| C12-15 Alkyl benzoate | 3.00 |
| Decyl cocoate | 4.00 |
| Ethylhexyl palmitate | 3.00 |
| Glyceryl stearate | 0.50 |
| Stearic acid | 0.50 |
| Tocopheryl acetate | 0.50 |

| Raw material (INCI) | % |
|---|---|
| B | |
| Cetearyl glucoside | 1.50 |
| Propylene glycol | 2.00 |
| Glycerin | 1.00 |
| Water | 76.80 |
| C | |
| Product from Example 4a | 5.00 |
| D | |
| Carbomer | 0.20 |
| Paraffinum liquidum (mineral oil) | 0.80 |
| E | |
| Sodium hydroxide | 0.50 |
| F | |
| Propylene glycol, diazolidinylurea, methylparaben, propylparaben | 0.50 |
| Perfume | 0.20 |

Preparation:

Heat phase A and phase B separately to 80° C. Add phase A to phase B with stirring. Incorporate phase C into the emulsion at 40° C. with stirring and homogenise until the pigment distribution is optimal. Add phase D at 35° C. and again homogenise briefly. Add phase E, check the pH and again homogenise briefly. Add phase F and stir until cold.

Formulation Example 11

W/O Sunscreen Lotion with Inorganic Filter, In Vitro SPF (Diffey Method) 8.7±1.6, UVA-PF 4.4±0.5

| Raw material (INCI) | % |
|---|---|
| A | |
| Cetyl PEG/PPG-10/1 Dimethicone | 2.50 |
| Stearoxy dimethicone | 0.25 |
| Ethylhexyl stearate | 12.75 |
| Ethylhexyl palmitate | 8.00 |
| Isohexadecane | 7.00 |
| Hydrogenated castor oil | 0.50 |
| Ceresin (microcrystalline wax) | 1.00 |
| B | |
| Product from Example 5b | 5.00 |
| C | |
| Water | 62.00 |
| Sodium chloride | 0.50 |
| Propylene glycol, diazolidinylurea, methylparaben, propylparaben | 0.50 |

Preparation:

Heat phase A to 80° C. Carefully incorporate the titanium dioxide (phase B) into the hot oil phase. Slowly add phase C to phase A/B with stirring (500 rpm, Mig stirrer). Homogenise for 2 minutes at 1600 rpm. Cool to about 40° C. with stirring (about 300 rpm) and again homogenise for 2 minutes at 1600 rpm.

Formulation Example 12

Antiageing Cream Gel—Intensive Cell Protection (O/W)

| Raw material | INCI | [%] |
|---|---|---|
| A | | |
| RonaCare ® Ectoin | ECTOIN | 2.00 |
| Titriplex ® III | DISODIUM EDTA | 0.10 |
| Water, demineralised | AQUA (WATER) | to 100 |
| B | | |
| Product from Example 5d | | 3.00 |
| Eusolex ® OS | ETHYLHEXYL SALICYLATE | 3.00 |
| Eusolex ® OCR | OCTOCRYLENE | 3.00 |
| RonaCare AP ® | Hydroxy Dimethoxybenzyl Malonate | 1.00 |
| Eusolex ® 9020 | BUTYL METHOXYDIBENZOYL-METHANE | 0.50 |
| Cegesoft C 24 | ETHYLHEXYL PALMITATE | 4.00 |

-continued

| Raw material | INCI | [%] |
|---|---|---|
| Sepiplus 400 | POLYSORBATE 20, POLYACRYLATE 13, POLYISOBUTENE C | 2.00 |
| Phenonip | PHENOXYETHANOL, BUTYLPARABEN, ETHYLPARABEN, PROPYLPARABEN, METHYLPARABEN | 0.70 |

Formulation Example 13

Illustrative formulations for cosmetic compositions which are obtained in the same way with titanium dioxide according to Example 3a, 3b, 3c, 3d, 4a, 4b, 4c, 5c, 5d, 5e, 5f, 5g or 5h (in each case referred to as titanium dioxide in the table) are indicated below. In addition, the INCI names of the commercially available compounds are indicated.

UV-Pearl, OMC stands for the composition with the INCI name: Water (for EU: Aqua), Ethylhexyl Methoxycinnamate, Silica, PVP, Chlorophenesin, BHT; this composition is commercially available under the name Eusolex® UV Pearls™ OMC from Merck KGaA, Darmstadt.

The other UV-Pearls indicated in the tables each have an analogous composition with OMC replaced by the UV filters indicated.

TABLE 1

W/O emulsions (data in % by weight)

| | 1-1 | 1-2 | 1-3 | 1-4 | 1-5 | 1-6 | 1-7 | 1-8 | 1-9 | 1-10 |
|---|---|---|---|---|---|---|---|---|---|---|
| Titanium dioxide | 3 | 2 | 5 | 10 | 7 | 4 | 15 | 1 | 3 | 3 |
| Butylmethoxydibenzoyl-methane | 5 | 3 | 2 | 1 | 2 | | | | 1 | 1 |
| Zinc oxide | | | | | | | | 5 | 2 | |
| UV-Pearl, OMC | 30 | 15 | 15 | 15 | 15 | 15 | 15 | 15 | 15 | 15 |
| Polyglyceryl-3 dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium dioxide | 3 | 5 | 2 | 4 | 3 | 1 | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Dihydroxyacetone | 5 | 3 | 2 | 5 | 1 | 3 | 7 | 2 |
| Polyglyceryl-3 dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |

TABLE 1-continued

| W/O emulsions (data in % by weight) | | | | | | | | |
|---|---|---|---|---|---|---|---|---|
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentaerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium dioxide | 1 | 2 | 5 | 1 | 3 | 4 | 5 | 2 | 3 | 3 | 3 |
| Benzylidene malonate polysiloxane | | | | 1 | | | | | 1 | 1 | |
| Methylene Bis-Benzotriazolyl Tetramethyl-butylphenol | | | | | | 1 | 2 | 1 | | | 1 |
| Zinc oxide | | | | | | | | 5 | 2 | | |
| UV-Pearl OMC | 5 | 5 | 5 | 5 | 7 | 5 | 5 | 5 | 5 | 5 | 8 |
| UV-Pearl, OCR | | 10 | | | | | | | | | 5 |
| UV-Pearl, Ethylhexyl-DimethylPABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |
| Butylmethoxy-dibenzoylmethane | | | | | | | | | | | 2 |
| UV-Pearl OMC, 4-Methylbenzylidene Camphor | 25 | | | | | | | | | | |
| Polyglyceryl-3 dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | to 100 | | | | | | | | | | |

TABLE 2

| O/W emulsions, data in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium dioxide | 3 | 2 | 5 | 2 | 5 | 2 | 5 | 2 | 5 | 3 |
| Methylene Bis-Benztriazolyl Tetramethylbutylphenol | | | | | | 1 | 2 | 1 | | |
| Butylmethoxydibenzoyl-methane | 3 | 3 | 3 | 3 | 3 | 3 | 3 | 3 | 3 | 3 |
| Bis(2-ethylhexyl) 2-(4-hydroxy-3,5-dimethoxy-benzylidene)malonate | 1 | 5 | 4 | | 6 | | 7 | | 2 | 1 |
| 4-Methylbenzylidene Camphor | 2 | | 3 | | 4 | | 3 | | 2 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium dioxide | 3 | 1 | 2 | 5 | 4 | 3 | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Butylmethoxydibenzoyl-methane | 3 | 3 | 3 | 3 | 3 | 3 | 3 | 3 |
| Bis(2-ethylhexyl) 2-(4-hydroxy-3,5-dimethoxy-benzylidene)malonate | 1 | 5 | 4 | | 6 | | 7 | |
| Zinc oxide | | | | 2 | | | | |
| UV-Pearl, OMC | 15 | 15 | 15 | 30 | 30 | 30 | 15 | 15 |
| 4-Methylbenzylidene Camphor | | | | 3 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| *Persea Gratissima* | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine | | | | | 1.8 | | | |
| Glycerin | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | 10 | 5 | 7 | 8 | 2 | 1 | 3 | 3 | 6 | 2 |
| Benzylidene malonate polysiloxane | 1 | 2 | | | | 1 | 1 | | 1 | 0.5 |
| Butylmethoxydibenzoyl-methane | 3 | 3 | 3 | 3 | 3 | 3 | 3 | 3 | 3 | 3 |
| Octocrylene | 1 | 5 | 4 | | 6 | | 7 | | 2 | 1 |
| Methylene Bis-Benztriazolyl Tetramethylbutylphenol | | | 1 | 2 | 1 | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |

TABLE 2-continued

O/W emulsions, data in % by weight

| Caprylic/Capric Triglyceride | 14 | 14 | 14 | 14 | 14 | 14 | 14 | 14 | 14 | 14 |
|---|---|---|---|---|---|---|---|---|---|---|
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| *Persea Gratissima* | 8 | 8 | 8 | 8 | 8 | 8 | 8 | 8 | 8 | 8 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glycerin | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

Gels, data in % by weight

| | 3-1 | 3-2 | 3-3 | 3-4 | 3-5 | 3-6 | 3-7 | 3-8 | 3-9 | 3-10 |
|---|---|---|---|---|---|---|---|---|---|---|
| Titanium dioxide | 5 | 2 | 5 | 1 | 1 | 1 | 1 | 1 | 3 | 3 |
| Butylmethoxydibenzoyl-methane | 2 | 2 | 2 | 2 | 2 | 2 | 2 | 2 | 2 | 2 |
| Dihydroxyacetone | 1 | 5 | 4 | | 6 | | 7 | | 2 | 1 |
| Benzylidene malonate polysiloxane | | | 1 | 1 | 2 | | | | 1 | 1 |
| Methylene Bis-Benzo-triazolyl Tetraomethylo-butylphenol | | 1 | | | | 1 | 2 | 1 | | |
| Zinc oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 3-11 | 3-12 | 3-13 |
|---|---|---|---|
| Titanium dioxide | 3 | 1 | 2 |
| Benzylidene malonate polysiloxane | | 1 | 0.5 |
| Methylene Bis-Benztriazolyl Tetramethylbutylphenol | 1 | 1 | 0.5 |
| Butylmethoxydibenzoylmethane | 2 | 2 | 2 |
| 2-(4-Hydroxy-3,5-dimethoxy-benzyliden)-malonsäure-bis-(2-ethyl-hexyl)ester | 1 | 5 | 4 |
| Zinc oxide | | | 2 |
| UV-Pearl, Ethylhexyl Mehtoxycinnamat | 15 | 15 | 15 |
| *Prunus Dulcis* | 5 | 5 | 5 |
| Tocopheryl Acetate | 0.5 | 0.5 | 0.5 |
| Caprylic/Capric Triglyceride | 3 | 3 | 3 |
| Octyldodecanol | 2 | 2 | 2 |
| Decyl Oleate | 2 | 2 | 2 |
| PEG-8 (and) Tocopherol (and) Ascorbyl Palmitate (and) Ascorbic Acid (and) Citric Acid | 0.05 | 0.05 | 0.05 |
| Sorbitol | 4 | 4 | 4 |
| Polyacrylamide (and) C13-14 Isoparaffin (and) Laureth-7 | 3 | 3 | 3 |
| Carbomer | | | |
| Propylparabene | 0.05 | 0.05 | 0.05 |
| Methylparabene | 0.15 | 0.15 | 0.15 |
| Allantoin | | | |
| Tromethamine | | | |

TABLE 3-continued

Gels, data in % by weight

| | | | |
|---|---|---|---|
| Water | ad 100 | ad 100 | ad 100 |
| Titanium dioxide | 3 | 1 | 2 |
| Benzylidene malonate polysiloxane | | 1 | 0.5 |
| Methylene Bis-Benztriazolyl Tetramethylbutylphenol | 1 | 1 | 0.5 |
| Butylmethoxydibenzoylmethane | 2 | 2 | 2 |
| Bis(2-ethylhexyl) 2-(4-hydroxy-3,5-dimethoxybenzylidene)malonate | 1 | 5 | 4 |
| Zinc oxide | | | 2 |
| UV-Pearl, Ethylhexyl Methoxycinnamate | 15 | 15 | 15 |
| Prunus Dulcis | 5 | 5 | 5 |
| Tocopheryl Acetate | 0.5 | 0.5 | 0.5 |
| Caprylic/Capric Triglyceride | 3 | 3 | 3 |
| Octyldodecanol | 2 | 2 | 2 |
| Decyl Oleate | 2 | 2 | 2 |
| PEG-8 (and) Tocopherol (and) Ascorbyl Palmitate (and) Ascorbic Acid (and) Citric Acid | 0.05 | 0.05 | 0.05 |
| Sorbitol | 4 | 4 | 4 |
| Polyacrylamide (and) C13-14 Isoparaffin (and) Laureth-7 | 3 | 3 | 3 |
| Carbomer | | | |
| Propylparaben | 0.05 | 0.05 | 0.05 |
| Methylparaben | 0.15 | 0.15 | 0.15 |
| Allantoin | | | |
| Tromethamine | | | |
| Water | to 100 | to 100 | to 100 |

| | 3-14 | 3-15 | 3-16 | 3-17 | 3-18 | 3-19 | 3-20 | 3-21 |
|---|---|---|---|---|---|---|---|---|
| Titanium dioxide | 1 | 5 | 3 | 1 | 2 | 8 | 12 | 1 |
| Butylmethoxydibenzoylmethane | 2 | 2 | 2 | 2 | 2 | 2 | 2 | 2 |
| UV-Pearl, OMC | 15 | 10 | | 10 | 10 | 10 | 15 | 10 |
| UV-Pearl, OCR | | | 10 | | | | | |
| UV-Pearl, OMC, Methylene Bis-Benzotriazolyl Tetramethylbutyl-5phenol | | 7 | | 6 | | | | |
| UV-Pearl, Ethylhexyl salicylate, Butylmethoxydibenzoylmethane | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 | a = aqueous gel

Formulation Example 14

Sunscreen Spray

| | | |
|---|---|---|
| A) | CERALUTION ® C; Sasol | 15.0% |
| B) | Product according to Example 2b | 5.0% |
| | Ethylhexyl Methoxycinnamate | 4.8% |
| | Ethylhexyl Salicylate | 4.8% |
| | Tocopheryl Acetate | 0.6% |
| | Cyclomethicone | 1.0% |
| | C12-15 Alkyl Benzoate | 2.5% |
| | Tridecyl Salicylate | 2.5% |
| C) | Water (Aqua), Deionised | 38.3% |
| | Water (Aqua), Deionised with 4% of Avicel CL 611 (Microcrystalline Cellulose (and) Cellulose Gum) | 25.0% |
| D) | Phenoxyethanol (and) Methylparaben (and) Ethylparaben (and) Butylparaben (and) Propylparaben (and) Isobutylparaben | 0.5% |
| E) | Fragrance q.s. | |

Preparation: phase B is slowly added to phase A at room temperature with stirring. Phase C is then added. Phases D and E are subsequently added.

INCI Ceralution® C:

Aqua (and) Capric/Caprylic triglyceride (and) Glycerin (and) Ceteareth-25 (and) Sodium Dicocoylethylenediamine PEG-15 Sulfate (and) Sodium Lauroyl Lactylate (and) Behenyl Alcohol (and) Glyceryl Stearate (and) Glyceryl Stearate Citrate (and) Gum Arabic (and) Xanthan Gum (and) Phenoxyethanol (and) Methylparaben (and) Ethylparaben (and) Butylparaben (and) Isobutylparaben

Formulation Example 15

Sunscreen Lotion (O/W); SPF 7.6 (Sun Protection Factor, Diffey Method)

|  | % |
|---|---|
| A | |
| Stearyl Alcohol (and) Steareth-7 (and) Steareth-10 | 3.00 |
| Glyceryl Stearate (and) Ceteth-20 | 3.00 |
| Cetearyl Octanoate | 15.50 |
| Glyceryl Stearate | 3.00 |
| Oleyl Oleate | 7.00 |
| Microwax | 1.00 |
| Caprylic/Capric Triglyceride | 6.00 |
| B | |
| Product according to Example 2c | 5.00 |
| Propylene Glycol | 4.00 |
| Preservative | q.s. |
| Water, demineralised | to 100.00 |

Preparation:
Stir titanium dioxide into phase B and heat to 80° C. Heat phase A to 75° C. Slowly add phase B to phase A with stirring, homogenise and cool with stirring.

Formulation Example 16

Sun Cream without Organ. Filters (W/O); In Vitro SPF (Diffey) 32+/−5

| Raw material | INCI | [%] |
|---|---|---|
| A | | |
| Water, demineralised | AQUA (WATER) | 3.40 |
| Polyethylene glycol 400 | PEG-8 | 4.00 |
| Pemulen TR-1 | ACRYLATES/C10-30 ALKYL ACRYLATE CROSSPOLYMER | 0.20 |
| Sodium hydroxide solution, 10% | SODIUM HYDROXIDE | 0.90 |
| STEPAN-MILD RM-1 | SODIUM STEARYL PHTHALAMATE | 1.00 |
| B1 | | |
| Ceraphyl 368 | ETHYLHEXYL PALMITATE | 10.00 |
| Zinc oxide | ZINC OXIDE | 3.00 |
| Imwitor 900 | GLYCERYL STEARATE | 0.50 |
| Jojoba oil | *BUXUS CHINENSIS* (JOJOBA OIL) | 1.00 |
| B2 | | |
| Germaben II | PROPYLENE GLYCOL, DIAZOLIDINYL, UREA, METHYLPARABEN, PROPYLPARABEN | 1.00 |
| Tegosoft TN | C12-15 ALKYL BENZOATE | 15.00 |
| Antaron V-216 | PVP/HEXADECENE COPOLYMER | 2.00 |
| Product according to Example 2d | | 8.00 |

Preparation:
1. Introduce water into vessel with heating means and stirrer (for example Eurostar digital mixer, IKA).
2. Add PEG-400, then introduce Pemulen TR-1 into the water phase with stirring until it is homogeneously distributed.
3. Add sodium hydroxide solution in order to activate the Pemulen TR-1, stir until a clear gel is formed.
4. Heat the water phase to 72-75° C.
5. Introduce Stepan-Mild RM1 at 70° C. at a low stirrer speed and heat to 70-72° C. Stir at this temperature for at least 15 minutes until the Stepanmild RM1 is well distributed.
6. Prepare oil phase in a separate vessel and heat to 75° C. Add Imwitor 900 and jojoba oil at 60° C. Continue heating and add oil phase B to the water phase at 75° C. at an increased stirrer speed and continue stirring for 10 minutes.
7. Prepare oil phase B2 in a further vessel. Heat Tegosoft TN and Antaron V-216 to 85° C. Add titanium dioxide at 75° C. and disperse for minutes until good pigment distribution has been achieved, homogenise if necessary. Add oil phase B2 to the emulsion from point 6 and continue emulsifying at 72-75° C. for 20-25 minutes.
9. Start cooling with moderate stirrer power.
10. Add Germaben II at <40° C. with stirring.
11. Homogenise in the U-Turrax for 5 minutes at 5000 rpm at t<35° C.
13. Cool to room temperature and deaerate.
14. Leave to rest overnight and package next day.

Formulation Example 17

Antiageing Cream Gel (O/W)

| Raw material | INCI | [%] |
|---|---|---|
| A | | |
| RonaCare AP | HYDROXY DIMETHOXYBENZYL MALONATE | 4.00 |
| Eusolex OCR | Octocrylene | 4.00 |
| Eusolex 9020 | Butyl Methoxydibenzoylmethane | 2.00 |
| Tegin | Glyceryl Stearate SE | 1.50 |
| Montanov S | Coco Glucoside; Coconut Alcohol | 1.50 |
| Dow Corning 246 | Cyclohexasiloxane | 5.00 |
| Cetiol A | Hexyl Laurate | 5.00 |
| Titanium Dioxide | | 1.00 |
| B | | |
| Water, demineralised | AQUA (WATER) | to 100 |
| Glycerin (87%) | Glycerin, Aqua | |
| Preservative | Preservative | q.s. |
| Titriplex II | Disodium EDTA | 0.10 |
| C | | |
| Simulgel EPG | Sodium polyacrylate (and) Sodium acryloyldimethyltaurate copolymer (and) polyisobutene (and) caprylyl capryl glucoside | 1.20 |
| Keltrol CG-SFT | Xanthan Gum | 0.20 |
| Dow Corning 245 | Cyclomethicone | 5.00 |
| D | | |
| Dow Corning HMW 220 | Divinyldimethicone/Dimethicone Copolymer (and) C12-13 Pareth-3 (and) C12-13 Pareth-23 | 3.00 |
| Perfume | Fragrance | q.s. |

Formulation Example 18

Environmental Block Cream Gel (O/W)

| Raw material | INCI | [%] |
|---|---|---|
| A | | |
| RonaCare AP | HYDROXY DIMETHOXYBENZYL MALONATE | 2.00 |
| Montanov 202 | ARACHIDYL ALCOHOL, BEHENYL ALCOHOL, ARACHIDYLGLUCOSIDE | 3.00 |
| X-Tend 226 | PHENYLETHYL BENZOATE | 8.00 |
| Pelemol BIP | ISOPROPYLPHTALIMIDE, BUTYLPHTALIDE | 2.00 |
| Permethyl 102A | ISOEICOSANE | 1.00 |
| Silkflo 366 NF | HYDROGENATED POLYDECENE | 1.00 |
| Eusolex 9020 | BUTYL METHOXYDIBENZOYL-METHANE | 1.00 |
| Titanium dioxide from Example 3a | | 1.00 |
| B | | |
| Glycerin (87% extra pure) | GLYCERIN | 3.00 |
| Water, demineralised | AQUA (WATER) | to 100 |
| C | | |
| Simulgel NS | HYDROXYETHYL ACRYLATE/SODIUM ACRYLOYLDIMETHYL-TAURATE COPOLYMER, SQUALANE, POLYSORBATE 60 | 2.05 |
| D | | |
| Germaben II | PROPYLENE GLYCOL, DIAZOLIDINYL UREA METHYLPARABEN, PROPYLPARABEN | 0.75 |
| NaOH (10%) | Aqua, Sodium Hydroxide | to pH 5.7 |

Formulation Example 19

"3 in 1" Care and Conditioning Shampoo

| Raw material | INCI | [%] |
|---|---|---|
| Water, demineralised | AQUA (WATER) | to 100 |
| Ronastar ® Noble Sparks | CALCIUM ALUMINUM BOROSILICATE, SILICA, CI 77891 (TITANIUM DIOXIDE), TIN OXIDE | 0.10 |
| Titanium dioxide from Example 3b | | 0.20 |
| Carbopol Aqua SF1 | ACRYLATES COPOLYMER | 8.00 |
| Texapon NSO | SODIUM LAURETH SULFATE | 40.00 |
| Sodium hydroxide solution, 10% | SODIUM HYDROXIDE | 0.00 |
| Tego Betain F 50 | COCAMIDOPROPYL BETAINE | 5.60 |
| ProtaFlor W25 | HYDROLYZED WHEAT PROTEIN, GLYCERIN, POLYQUATERNIUM-7 | 1.00 |
| Dow Corning 193 Fluid | PEG-12 DIMETHICONE | 3.00 |
| 0.1% FD&C Yellow No. 5 in water | AQUA (WATER), CI 19140 (FD&C YELLOW NO. 5) | 1.00 |
| Frag 280847 Vert & Pampelmousse | PARFUM | 0.40 |
| Brondinox L | Propylene Glycol, 5-BROMO-5-NITRO-1,3-DIOXANE | 0.30 |
| Oxynex ST Liquid | Diethylhexylsyringelydene Malonate, Capric Caprylic Triglyceride | 0.10 |

Formulation Example 20

Antiageing Moisture Care Intensive O/W

| Ingredients | INCI | [%] |
|---|---|---|
| A | | |
| Eusolex ® OCR | OCTOCRYLENE | 10.00 |
| Eusolex ® 9020 | BUTYL METHOXYDIBENZOYL-METHANE | 5.00 |
| Tego Care 450 | (2)POLYGLYCERYL-3 METHYL-GLUCOSE DISTEARATE | 2.00 |
| Tegosoft TN | C12-15 ALKYL BENZOATE | 4.50 |
| Crodaderm S | SUCROSE POLYSOYATE | 2.00 |
| Syncrowax HGLC | C18-36 ACID TRIGLYCERIDE | 1.00 |
| Softisan 100 | HYDROGENATED COCO-GLYCERIDES | 1.00 |
| Antaron V-216 | PVP/HEXADECENE COPOLYMER | 1.00 |
| Shea butter | *BUTYROSPERMUM PARKII* (SHEA BUTTER) | 0.50 |
| Dow Corning 200 (100 cs) | DIMETHICONE | 2.00 |
| Tween 20 | POLYSORBATE 20 | 0.25 |
| RonaCare AP | Hydroxy Dimethoxybenzyl Malonate | 0.20 |
| Propyl 4-hydroxybenzoate | PROPYLPARABEN | 0.05 |
| B | | |
| Titanium dioxide from Example 3a | TITANIUM DIOXIDE, SILICA | 1.00 |
| RonaCare ® Ectoin | ECTOIN | 0.30 |
| 1,3-Butanediol | BUTYLENE GLYCOL | 5.00 |
| Glycerin, anhydrous | GLYCERIN | 1.75 |
| Titriplex ® III | DISODIUM EDTA | 0.05 |
| Water, demineralised | AQUA (WATER) | 61.60 |
| Methyl 4-hydroxybenzoate | METHYLPARABEN | 0.15 |
| C | | |
| Pemulen TR-2 | ACRYLATES/C10-30 ALKYL ACRYLATE CROSSPOLYMER | 0.15 |
| Tegosoft TN | C12-15 ALKYL BENZOATE | 0.50 |
| Sodium hydroxide, 10% solution | SODIUM HYDROXIDE | q.s. |
| Fragrance | PARFUM | q.s. |

Formulation Example 21

Extra Strong Sunscreen with Free-Radical Protection O/W

| Raw material | INCI | [%] |
|---|---|---|
| A | | |
| Titanium dioxide from Example 6b | | |
| Miglyol 8810 | BUTYLENE GLYCOL DICAPRYLATE/DICAPRATE | 8.00 |
| Dehymuls PGPH | POLYGLYCERYL-2 DIPOLYHYDROXY-STEARATE | 1.00 |

-continued

| Raw material | INCI | [%] |
|---|---|---|
| Eusolex ® OCR | OCTOCRYLENE | 10.00 |
| Eusolex ® 9020 | BUTYL METHOXYDIBENZOYL-METHANE | 4.00 |
| Eusolex ® 4360 | BENZOPHENONE-3 | 4.00 |
| Emulgade F | SODIUM CETEARYL SULFATE, CETEARYL ALCOHOL, PEG-40 CASTOR OIL | 3.00 |
| Tegin | GLYCERYL STEARATE SE | 1.50 |
| Syncrowax HGLC | C18-36 ACID TRIGLYCERIDE | 1.50 |
| Softisan 100 | HYDROGENATED COCO-GLYCERIDES | 1.50 |
| Dow Corning 345 | CYCLOMETHICONE | 6.00 |
| X-Tend 226 | PHENYLETHYL BENZOATE | 4.50 |
| Antaron V-216 | PVP/HEXADECENE COPOLYMER | 1.00 |
| RonaCare AP | Hydroxy Dimethoxybenzyl Malonate | 0.50 |
| Propyl 4-hydroxybenzoate | PROPYLPARABEN | 0.05 |
| B | | |
| Eusolex ® 232 | PHENYLBENZIMIDAZOLE SULFONIC ACID | 3.00 |
| Triethanolamine | TRIETHANOLAMINE | 1.60 |
| Keltrol RD | XANTHAN GUM | 0.20 |
| RonaCare ® Ectoin | ECTOIN | 0.10 |
| Glycerin, anhydrous | GLYCERIN | 5.00 |
| Titriplex ® III | DISODIUM EDTA | 0.05 |
| Methyl 4-hydroxybenzoate | METHYLPARABEN | 0.15 |
| Water, demineralised | AQUA (WATER) | 39.35 |
| Perfume oil (q.s.) | PARFUM | 0.00 |

Formulation Example 22

Moisturising Sun Milk with Cell Protection O/W

| Raw material | INCI | [%] |
|---|---|---|
| A | | |
| Titanium dioxide from Example 6c | | 2.00 |
| Eusolex ® OCR | OCTOCRYLENE | 9.00 |
| Eusolex ® 9020 | BUTYL METHOXYDIBENZOYL-METHANE | 2.00 |
| Arlacel 165 VP | GLYCERYL STEARATE, PEG-100 STEARATE | 2.00 |
| Amphisol K | POTASSIUM CETYL PHOSPHATE | 1.50 |
| Lanette 16 | CETYL ALCOHOL | 1.00 |
| Stearic acid | STEARIC ACID | 1.00 |
| Shea butter solid | *BUTYROSPERMUM PARKII* (SHEA BUTTER) | 0.50 |
| Dow Corning 245 | CYCLOMETHICONE | 2.50 |
| Arlamol HD | ISOHEXADECANE | 1.00 |
| Dow Corning 200 (10 cs) | DIMETHICONE | 0.50 |
| Antaron V-216 | PVP/HEXADECENE COPOLYMER | 1.00 |
| Vitamin E acetate (DL-alpha-tocopherol acetate)/Ph Eu | TOCOPHERYL ACETATE | 0.50 |
| B | | |
| Eusolex ® UV-Pearls OMC | AQUA (WATER), ETHYLHEXYL METHOXYCINNAMATE, SILICA, PVP, CHLORPHENESIN, BHT | 3.00 |
| RonaCare ® Ectoin | ECTOIN | 0.15 |
| Glycerin, anhydrous | GLYCERIN | 5.00 |
| Propylene glycol, 1,2- | PROPYLENE GLYCOL | 4.00 |
| Keltrol CG-SFT | XANTHAN GUM | 0.10 |
| Water, demineralised | AQUA (WATER) | to 100 |

-continued

| Raw material | INCI | [%] |
|---|---|---|
| C | | |
| Pemulen TR-2 | ACRYLATES/C10-30 ALKYL ACRYLATE CROSSPOLYMER | 0.05 |
| Cetiol LC | COCO-CAPRYLATE/CAPRATE | 0.50 |
| Triethanolamine | TRIETHANOLAMINE | |
| Preservatives, q.s. | PHENOXYETHANOL, ISOPROPYL-PARABEN, ISOBUTYLPARABEN, BUTYLPARABEN | |
| Perfume oil (q.s.) | PARFUM | |

Formulation Example 23

Sun Milk with Skin Protection Balance O/W

| Ingredients | INCI | [%] |
|---|---|---|
| A | | |
| Titanium dioxide from Example 6a | | 2.00 |
| Miglyol 8810 | BUTYLENE GLYCOL DICAPRYLATE/DICAPRATE | 2.00 |
| Dehymuls PGPH | POLYGLYCERYL-2 DIPOLY-HYDROXYSTEARATE | 0.50 |
| Eusolex ® OCR | OCTOCRYLENE | 4.50 |
| Eusolex ® 2292 | ETHYLHEXYL METHOXY-CINNAMATE, BHT | 0.50 |
| Eusolex ® 9020 | BUTYL METHOXYDIBENZOYL-METHANE | 2.00 |
| Imwitor 372 P | GLYCERYL STEARATE CITRATE | 2.50 |
| Lanette 18 | STEARYL ALCOHOL | 1.50 |
| Softisan 100 | HYDROGENATED COCO-GLYCERIDES | 1.00 |
| Cetiol OE | DICAPRYLYL ETHER | 3.00 |
| Eutanol G | OCTYLDODECANOL | 3.00 |
| Dow Corning 345 | CYCLOMETHICONE | 2.50 |
| Antaron V-216 | PVP/HEXADECENE COPOLYMER | 0.50 |
| Vitamin E acetate | TOCOPHERYL ACETATE | 0.50 |
| Propyl 4-hydroxybenzoate | PROPYLPARABEN | 0.05 |
| B | | |
| Keltrol RD | XANTHAN GUM | 0.25 |
| RonaCare ® Ectoin | ECTOIN | 0.10 |
| Glycerin, anhydrous | GLYCERIN | 5.00 |
| Titriplex ® III | DISODIUM EDTA | 0.05 |
| Water, demineralised | AQUA (WATER) | to 100 |
| Methyl 4-hydroxybenzoate | METHYLPARABEN | 0.15 |
| C | | |
| Cetiol OE | DICAPRYLYL ETHER | 0.50 |
| Pemulen TR-2 | ACRYLATES/C10-30 ALKYL ACRYLATE CROSSPOLYMER | 0.10 |
| Triethanolamine | TRIETHANOLAMINE | 0.70 |
| Fragrance | PARFUM | q.s. |

Figure 1:
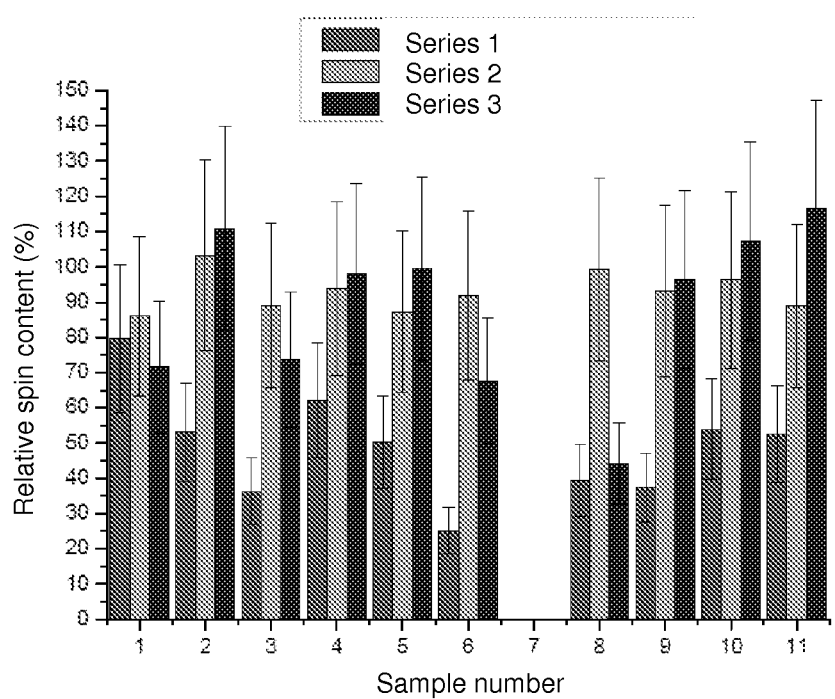
FIG. 1 shows the results of the continuous wave GPR measurements in accordance with Example 10 (method 10a). The spin concentration of the respective sample is indicated.
Figure 2:
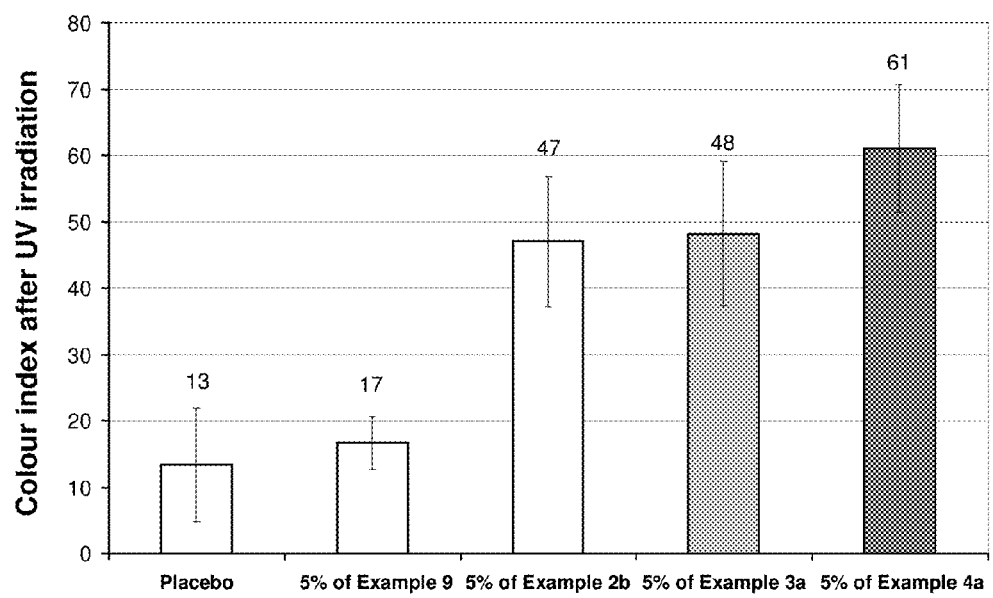
FIG. 2 shows the results of the efficacy test in vivo against photooxidative stress of the skin, induced by UVA irradiation (method 10h). The colour index after UV irradiation of the respective sample is indicated.
Figure 3:
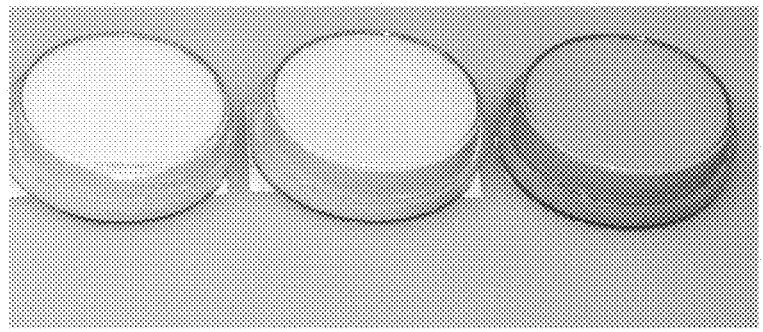
FIG. 3 shows the results of the determination of the product colour in formulation for three formulations (method 10c).

The invention claimed is:

1. A UV protection agent, where the UV protection essentially emanates from a particulate metal oxide, comprising a particulate metal oxide, which is titanium dioxide,
   wherein
   the crystallite size of the particulate titanium dioxide in the particulate UV protection agent, determined by the Scherrer method, is 8 to 50 nm, and the dimensions of the particulate titanium dioxide, which can be determined in a transmission electron microscope, are a length of 20 to 60 nm and a width of 8 to 30 nm, and
   the titanium dioxide carries a first coating consisting essentially of aluminum compounds and a second coating consisting essentially of one or more manganese compounds.

2. A UV protection agent according to claim 1, wherein the one or more manganese compounds are selected from the group consisting of the oxides, hydroxides, phosphates, sulfates and fatty acid salts of manganese.

3. An aqueous or oily dispersion comprising a particulate UV protection agent according to claim 1 and water or an oil.

4. A composition having light-protection properties comprising a carrier and at least one UV protection agent according to claim 1.

5. A composition having light-protection properties according to claim 4, which is suitable for the protection of body cells against oxidative stress, for reducing skin ageing, and which optionally comprises one or more antioxidants.

6. A UV filter comprising a carrier and a particulate UV protection agent according to claim 1.

7. A process for preparing a particulate UV protection agent according to claim 1, comprising
   a) subjecting a particulate titanium dioxide to hydrothermal treatment and
   b) subsequently applying a first coating consisting essentially of aluminum compounds and a second coating consisting essentially of one or more manganese compounds.

8. A process according to claim 7,
   wherein step a) is carried out in a sealed container at 40 to 360° C.;
   or
   wherein step b) is carried out as a sol-gel process, in which a manganese sulfate solution is optionally added to a suspension of the titanium dioxide;
   or
   wherein step b) is carried out at a pH kept constant in the range from pH=2 to pH=11;
   or
   wherein step b) is carried out at elevated temperature;
   or
   wherein a hydrophobicising layer is applied in an after-treatment.

9. A process for preparing a composition according to claim 4, comprising mixing said entity with a cosmetically or dermatologically suitable vehicle.

10. A UV protection agent according to claim 1, which possesses the property of a spin concentration of 25 to 40% after having been combined with 2,2-diphenyl-1-picrylhydrazyl for three minutes, wherein said property has been measured by spectra recordation on a Bruker E500 X Band cw spectro-meter at room temperature.

11. A food comprising a UV protection agent according to claim 1.

12. A UV protection agent according to claim 1, wherein the titanium dioxide is doped with a metal.

13. A UV protection agent according to claim 1, wherein the titanium dioxide is doped with Fe.

14. A cosmetic composition, comprising a cosmetically acceptable carrier and a UV protection agent according to claim 13.

15. A cosmetic composition, comprising a cosmetically acceptable carrier and a UV protection agent according to claim 1.

* * * * *